(12) United States Patent
Zhu et al.

(10) Patent No.: US 11,143,652 B2
(45) Date of Patent: Oct. 12, 2021

(54) ADSORPTION MECHANISM, CLEANING DEVICE, CHEMILUMINESCENCE DETECTOR AND CLEANING METHOD

(71) Applicant: Shenzhen New Industries Biomedical Engineering Co., Ltd., Guangdong (CN)

(72) Inventors: Liang Zhu, Guangdong (CN); Li Yin, Guangdong (CN); Yi Hu, Guangdong (CN); Dingping Ban, Guangdong (CN); Wanguan Yi, Guangdong (CN); Shuai Tong, Guangdong (CN)

(73) Assignee: Shenzhen New Industries Biomedical Engineering Co., Ltd., Guangdong (CN)

( * ) Notice: Subject to any disclaimer, the term of this patent is extended or adjusted under 35 U.S.C. 154(b) by 223 days.

(21) Appl. No.: 16/252,744

(22) Filed: Jan. 21, 2019

(65) Prior Publication Data

US 2020/0080998 A1  Mar. 12, 2020

(30) Foreign Application Priority Data

Sep. 11, 2018 (CN) .......................... 201811057621.8

(51) Int. Cl.
  *G01N 33/543* (2006.01)
  *G01N 21/76* (2006.01)
  *G01N 35/00* (2006.01)
  *G01N 35/02* (2006.01)
  (Continued)

(52) U.S. Cl.
  CPC ....... *G01N 33/54333* (2013.01); *G01N 21/76* (2013.01); *G01N 35/0098* (2013.01);
  (Continued)

(58) Field of Classification Search
  CPC ... G01N 2035/1006; G01N 2035/0437; G01N 2035/00801; G01N 2035/00564;
  (Continued)

(56) References Cited

U.S. PATENT DOCUMENTS

| | | | | |
|---|---|---|---|---|
| 5,888,835 A | * | 3/1999 | Bushnell | .......... G01N 33/54326 436/526 |
| 2014/0099240 A1 | * | 4/2014 | Misono | ................. B01L 3/0217 422/514 |

FOREIGN PATENT DOCUMENTS

| | | |
|---|---|---|
| CN | 102419375 A | 4/2012 |
| CN | 103399161 A | 11/2013 |

(Continued)

*Primary Examiner* — Samuel P Siefke
*Assistant Examiner* — Oyeleye Alexander Alabi
(74) *Attorney, Agent, or Firm* — Gang Yu

(57) ABSTRACT

The present disclosure relates to, a magnetic microbeads adsorption mechanism, which is configured to adsorb a magnetic microbeads in a reaction cup and is provided with a cup inlet station and a cup outlet station; the magnetic microbeads adsorption mechanism includes a pedestal, a turntable and multiple magnetic adsorption components; the turntable is rotatably mounted on the pedestal; the turntable can drive the reaction cup to rotate around a central axis of the turntable; the multiple magnetic adsorption components are arranged on a mounting circumference of the pedestal at intervals; the mounting circumference and rotation track of the reaction cup are concentrically arranged; and during a process when the reaction cup rotates from the cup inlet station to the cup outlet station, the adsorption height of the magnetic microbeads relative to cup bottom of the reaction cup can be changed.

19 Claims, 14 Drawing Sheets

(51) Int. Cl.
*G01N 35/04* (2006.01)
*G01N 35/10* (2006.01)

(52) U.S. Cl.
CPC . *G01N 35/025* (2013.01); *G01N 2035/00564* (2013.01); *G01N 2035/00801* (2013.01); *G01N 2035/0437* (2013.01); *G01N 2035/1006* (2013.01)

(58) Field of Classification Search
CPC .. G01N 35/025; G01N 35/0098; G01N 21/76; G01N 33/54333
See application file for complete search history.

(56) References Cited

FOREIGN PATENT DOCUMENTS

| CN | 203337661 | U | | 12/2013 | |
| --- | --- | --- | --- | --- | --- |
| CN | 203426088 | U | | 2/2014 | |
| CN | 105259357 | A | | 1/2016 | |
| CN | 104777321 | B | * | 7/2016 | ........... G01N 35/025 |
| CN | 105891113 | A | | 8/2016 | |
| CN | 205991942 | U | | 3/2017 | |
| CN | 206046608 | | * | 3/2017 | ............... B08B 9/08 |
| CN | 206046608 | U | | 3/2017 | |
| CN | 206132787 | U | | 4/2017 | |
| CN | 107144689 | | * | 9/2017 | ........... G01N 33/543 |
| CN | 107144689 | A | | 9/2017 | |
| CN | 107262444 | | * | 9/2017 | ............... B08B 3/10 |
| CN | 107262444 | A | | 10/2017 | |
| CN | 107377563 | A | | 11/2017 | |
| CN | 207148132 | U | | 3/2018 | |
| CN | 207148132 | U | * | 3/2018 | ............. G01N 35/00 |
| CN | 207423982 | U | | 5/2018 | |
| CN | 207816996 | U | | 9/2018 | |
| CN | 110076154 | A | | 8/2019 | |
| CN | 110082549 | A | | 8/2019 | |

* cited by examiner

ADSORPTION MECHANISM, CLEANING DEVICE, CHEMILUMINESCENCE DETECTOR AND CLEANING METHOD

TECHNICAL FIELD

Embodiments of the present disclosure relate to a technical field of medical appliances, and more particularly, to a magnetic microbeads adsorption mechanism, a cleaning device including the magnetic microbeads adsorption mechanism, a chemiluminescence detector including the cleaning device and a cleaning method.

BACKGROUND

An automated chemiluminescence immunoassay analyzer is an instrument capable of performing immunological quantitative analysis on a body fluid of a patient, and is used for detecting items such as a tumor marker and a cardiovascular disease. It mainly includes a sample adding module, an incubation module, a cleaning module, a measurement module and a software control module. During the whole operation, a to-be-analyzed body fluid sample is added to a reaction cup by using the sample adding module first and then a reaction reagent of a magnetic bead adsorbed with an antigen or an antibody is added to the reaction cup; after an incubation reaction of the incubation module, the sample and the reagent need to enter the cleaning module for cleaning, so that unreacted body fluid sample and reagent is removed and only a complex connected with the magnetic bead after the reaction is remained; and at last; the complex is put into the measurement module for measurement to obtain a measurement result.

During cleaning, it is general to adsorb the magnetic beads to cup wall of the reaction cup via an external magnetic field and then remove unreacted substances in the reaction cup to achieve the cleaning purpose. In an existing cleaning device, magnet components are arranged at a side of the reaction cup generally in the external magnetic field. However, the requirements on height of the magnetic bead in the reaction cup is not consistent in different cleaning stages, and different reaction liquid height is present in the reaction cup in the different cleaning stages, The heights of existing magnet components are set to be uniform and different magnet heights do not designed according to different requirements, resulting in that the magnetic beads are lost seriously and the accuracy of a detection result is affected.

SUMMARY

A technical problem to be solved by the present disclosure is to provide a magnetic microbeads adsorption mechanism, a cleaning device, a chemiluminescence detector and a cleaning device to improve the testing accuracy on the basis of guaranteeing the cleaning effect.

A magnetic microbeads adsorption mechanism, configured to adsorb a magnetic microbeads in reaction cup and provided with a cup inlet station and a cup outlet station, includes a pedestal, a turntable and multiple magnetic adsorption components; the turntable is rotatably mounted on the pedestal and is configured to support the reaction cup; the turntable can drive the reaction cup to rotate around a central axis of the turntable; the multiple magnetic adsorption components are arranged at intervals on a mounting circumference of the pedestal; and the mounting circumference and rotation track of the reaction cup is concentrically arranged.

Wherein the reaction cup can enter the turntable from the cup inlet station and move away the turntable from the cup outlet station; the magnetic microbeads is provided with adsorption position on cup wall of the reaction cup, the distance from the adsorption position to a cup bottom of the reaction cup is the adsorption height, and during a process when the reaction cup rotates from the cup inlet station to the cup outlet station, the adsorption height of the magnetic microbeads can be changed.

A cleaning device includes the above-mentioned magnetic microbeads adsorption mechanism.

A chemiluminescence detector includes the above-mentioned cleaning device.

A cleaning method applied to a turntable type cleaning device to clean a magnetic microbeads in a reaction cup includes the following steps.

The reaction cup added with a sample for a first time and injected with a cleaning solution enters from a cup inlet station of the cleaning device and rotates around a central axis of the cleaning device.

Primary cleaning is performed, where the magnetic microbeads is adsorbed to the reaction cup and waste liquor is extracted, then the cleaning solution is injected after the waste liquor is extracted and the reaction cup is vibrated.

Secondary cleaning is performed, where an adsorption position of the magnetic microbeads on the reaction cup is enabled to gradually get close to cup bottom of the reaction cup and then the waste liquor is extracted.

The reaction cup rotated to a cup outlet station of the cleaning device for a first time is conveyed to a measurement chamber.

A cleaning method applied to a turntable type cleaning device to clean a magnetic microbeads in a reaction cup includes the following steps.

The reaction cup added with a sample for a first time and injected with a cleaning solution enters from a cup inlet station of the cleaning device and rotates around a central axis of the cleaning device.

Primary cleaning is performed, where a magnetic microbeads is adsorbed to the reaction cup and waste liquor is extracted, then the cleaning solution is injected after the waste liquor is extracted and the reaction cup is vibrated.

Secondary cleaning is performed, where an adsorption position of the magnetic microbeads on the reaction cup is enabled to gradually get close to cup bottom of the reaction cup and then the waste liquor is extracted.

The distance of the adsorption position of the magnetic microbeads on the reaction cup is enabled to be lowest relative to the cup bottom of the reaction cup.

The reaction cup rotated to the cup outlet station of the cleaning device for a first time is conveyed to a reaction disc to add the sample for a second time.

The reaction cup added with the sample for a second time enters the turntable from the cup inlet station of the cleaning device, and after the primary cleaning and the secondary cleaning are performed, the reaction cup rotated to the cup outlet station of the cleaning device for the second time is conveyed to a measurement chamber.

A cleaning method applied to a turntable type cleaning device to clean a magnetic microbeads in a reaction cup includes the following steps.

The reaction cup added with a sample for a first time and injected with a cleaning solution enters from a cup inlet station of the cleaning device and rotates around a central axis of the cleaning device.

Primary cleaning is performed, where a magnetic microbeads is adsorbed to the reaction cup and waste liquor is extracted, then the cleaning solution is injected after the waste liquor is extracted and the reaction cup is vibrated.

Secondary cleaning is performed, where an adsorption position of the magnetic microbeads on the reaction cup is enabled to gradually get close to a cup bottom of the reaction cup and then the waste liquor is extracted.

After multiple times of primary cleaning and secondary cleaning, the reaction cup rotated to the cup outlet station of the cleaning device is conveyed to a measurement chamber.

According to the magnetic microbeads adsorption mechanism, the cleaning device, the chemiluminescence detector and the cleaning method provided by the present disclosure, the adsorption height of the magnetic microbeads can be changed during the process when the reaction cup is rotated around the central axis of the turntable, so on the basis of guaranteeing the cleaning effect of the magnetic microbeads, the loss of the magnetic microbeads in a subsequent waste liquor extraction process can be effectively prevented; and meanwhile, the requirements on the magnetic microbeads during different cleaning stages can be guaranteed, so that the magnetic microbeads is fully reacted with a detection reagent added during measurement and detection, and thus the accuracy of a measurement result is improved.

DETAILED DESCRIPTION OF THE EMBODIMENTS

In order to understand the present disclosure conveniently, the present disclosure will be described below more comprehensively with reference to relevant accompanying drawings. Preferred embodiments of the present disclosure are given in the accompanying drawings. However, the present disclosure may be implemented in many different forms and is not limited to the embodiments described herein. On the contrary, the purposes for providing these embodiments are to understand the contents disclosed in the present disclosure more completely and thoroughly.

It is to be noted that, when an element is "fixed" on another element, it may be directly on another element or also may has a middle element. When an element is "connected" to another element, it may be directly connected to another element or may be simultaneously has a middle element. As used herein, the terms "inside", "outside", "left", "right" and similar expressions are only for illustration but not express a unique embodiment.

Figure 1:
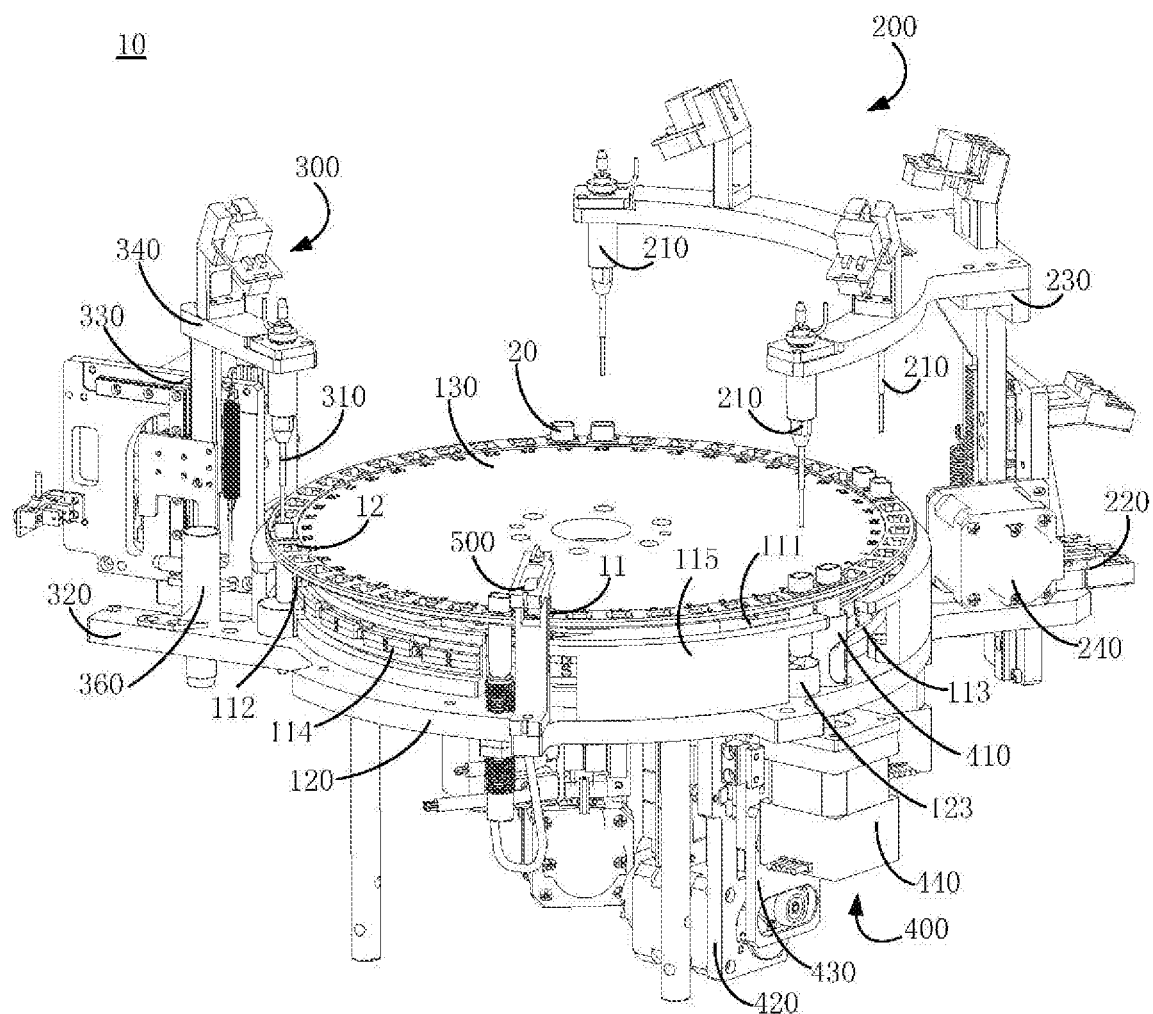
FIG. 1 is a stereoscopic diagram of a cleaning device provided by an embodiment.

Referring to FIG. 1, a cleaning device 10 is configured to clean a magnetic microbeads 30 in a reaction cup 20; the cleaning device 10 includes a magnetic microbeads adsorption mechanism 100, a primary cleaning mechanism 200, a secondary cleaning mechanism 300, mixing mechanisms 400 and a turntable 130; the primary cleaning mechanism 200, the secondary cleaning mechanism 300, the mixing mechanisms 400 and the turntable 130 all are mounted on the magnetic microbeads adsorption mechanism 100; the turntable 130 is configured to support the reaction cup 20 and drives the reaction cup 20 to rotate around a central axis of the turntable 130; multiple supporting stations are provided on an outer circumference of the turntable 130 uniformly at intervals along the periphery; and the reaction cup 20 is accommodated (e.g., inserted) into the supporting stations. During the process when the reaction cup 20 is rotated around the central axis of the turntable 130, the whole cleaning device 10 cleans the magnetic microbeads 30 to remove interferential impurities and the interferential impurities are prevented from affecting a subsequent testing result.

Figure 2:
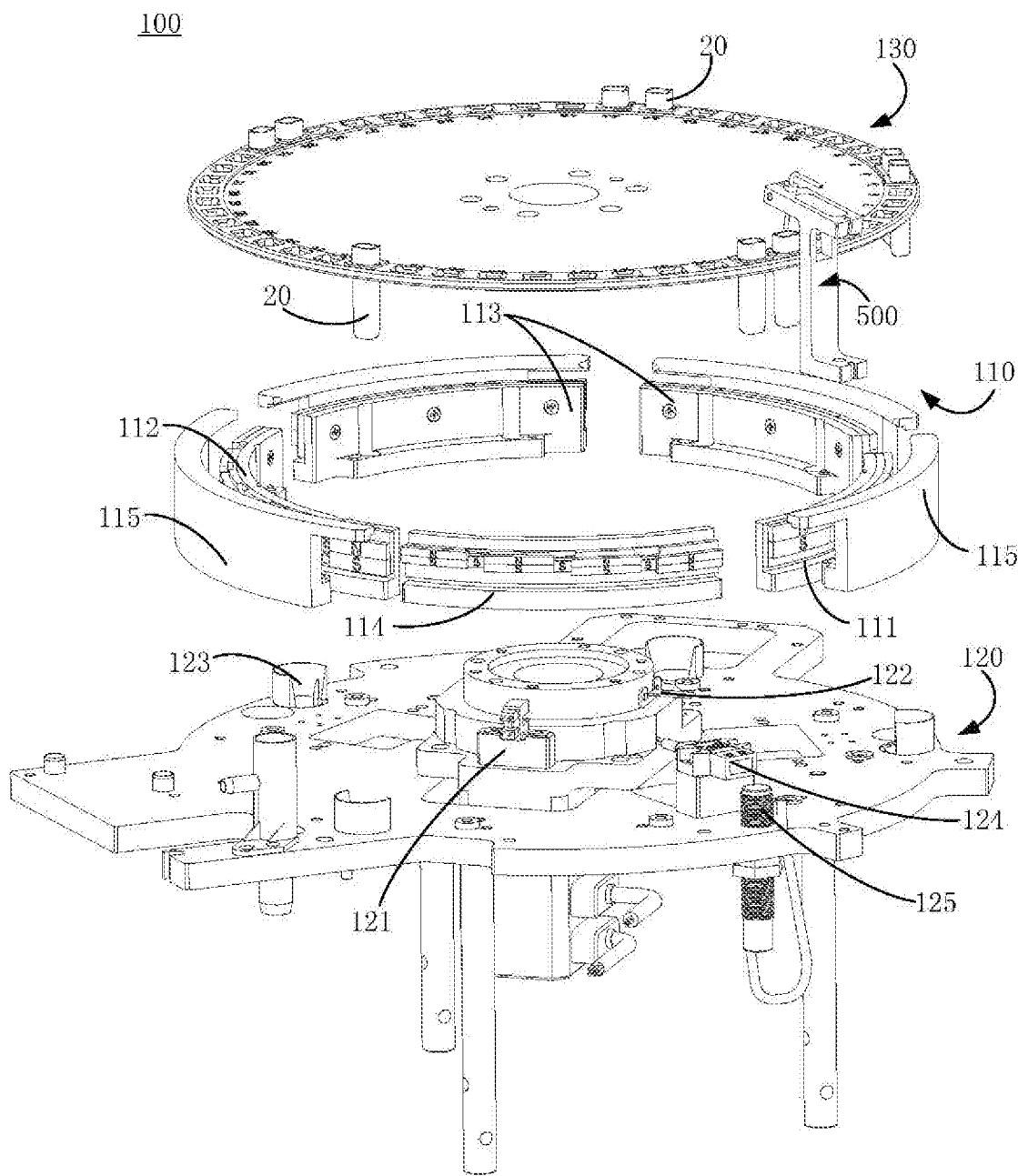
FIG. 2 is an exploded schematic diagram of a magnetic microbeads adsorption mechanism in FIG. 1.
Figure 3:
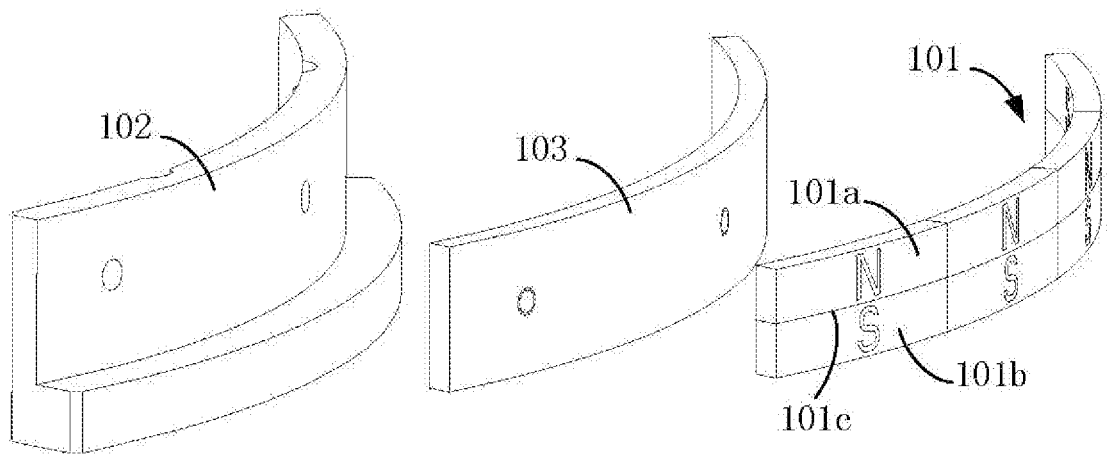
FIG. 3 is an exploded schematic diagram of a first magnetic adsorption component in FIG. 2.
Figure 4:
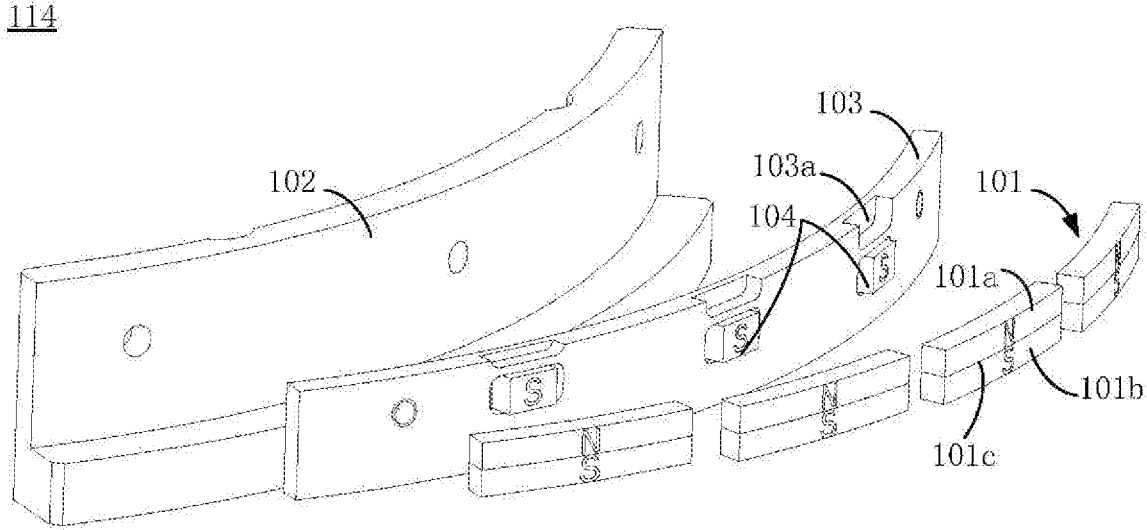
FIG. 4 is an exploded schematic diagram of a pull-down component in FIG. 2.
Figure 5:
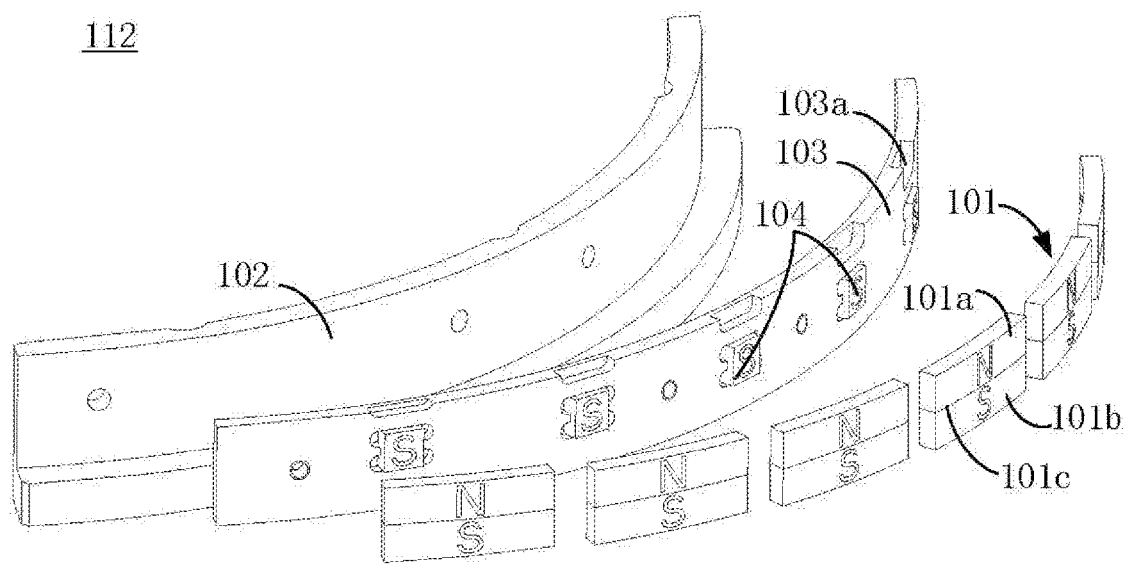
FIG. 5 is an exploded schematic diagram of a second magnetic adsorption component in FIG. 2.
Figure 6:
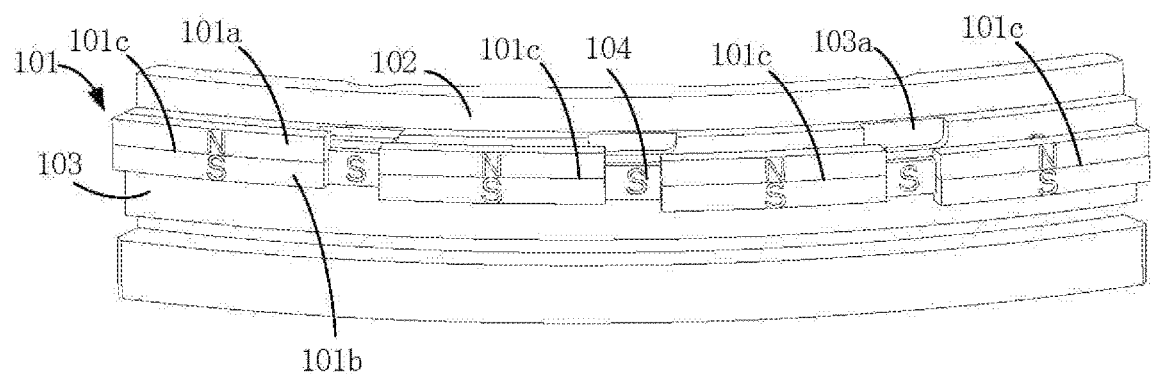
FIG. 6 is a schematic diagram showing an assembly structure of a pull-down component in FIG. 2.
Figure 7:
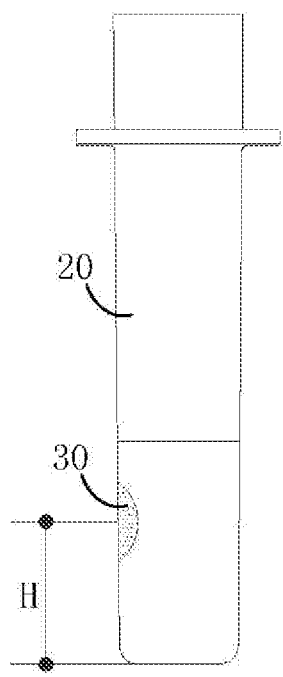
FIG. 7 is a schematic diagram of an adsorption position of a magnetic microbeads when a reaction cup is rotated to a head end of a second magnetic adsorption component.
Figure 8:
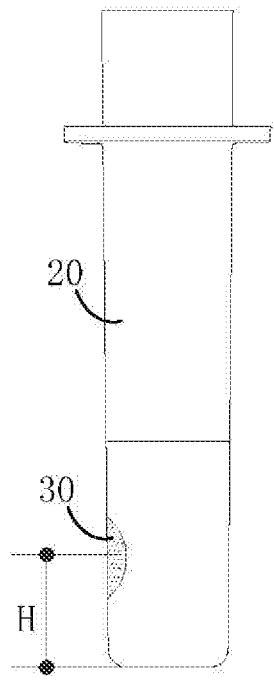
FIG. 8 is a schematic diagram of an adsorption position of a magnetic microbeads when a reaction cup is rotated to a middle portion of a second magnetic adsorption component.
Figure 9:
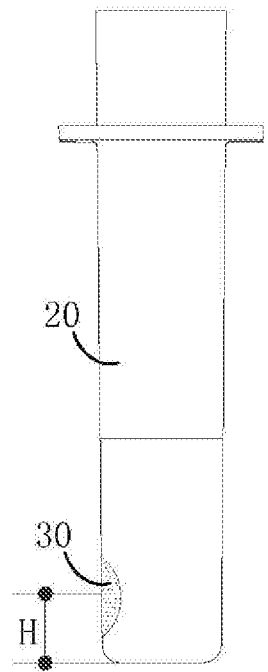
FIG. 9 is a schematic diagram of an adsorption position of a magnetic microbeads when a reaction cup is rotated to a tail end of a second magnetic adsorption component.

Referring to FIG. 1 and FIG. 2 simultaneously, the magnetic microbeads adsorption mechanism 100 includes a pedestal 120 and multiple magnetic adsorption components 110; and the multiple magnetic adsorption components 110 include a first magnetic adsorption component 111, a second magnetic adsorption component 112 and a middle magnetic adsorption component 113. For example, one first magnetic adsorption component 111 and one second magnetic adsorption component 112 is provided and two middle magnetic adsorption components 113 are provided. Of course, there may also be one middle magnetic adsorption component 113 or more than three middle magnetic adsorption components 113 and the like. The pedestal 120 is provided with a mounting circumference thereon. The first magnetic adsorption component 111, the middle magnetic adsorption components 113 and the second magnetic adsorption component 112 are arranged on the mounting circumference sequentially at intervals along the periphery. The mounting circumference and rotation track of the reaction cup 20 is concentrically provided. When the reaction cup 20 is rotated, the end to which the reaction cup 20 is close first is a head end of each of the magnetic adsorption components 110, and the end from which the reaction cup 20 is away at last is a tail end of each of the magnetic adsorption components 110. The magnetic microbeads adsorption mechanism 100 is further provided with a cup inlet station 11 and a cup outlet station 12. The reaction cup 20 can enter the turntable 130 from the cup inlet station 11; and when rotating to the cup outlet station 12 along with the turntable 130, the reaction cup 20 may move away the turntable 130 from the cup outlet station 12. Specifically, the cup inlet station 11 is arranged close to a head end of the first magnetic adsorption component 111, and the cup outlet station 12 is arranged close to a tail end of the second magnetic adsorption component 112. Along rotation direction (e.g., counterclockwise direction) of the reaction cup 20, the first magnetic adsorption component 111, the middle magnetic adsorption components 113 and the second magnetic adsorption component 112 are arranged sequentially in a head and tail opposite manner, i.e., the tail end of the first magnetic adsorption component 111 is opposite to the head end of the middle magnetic adsorption components 113, the tail end of the middle magnetic adsorption components 113 is opposite to the head end of the second magnetic adsorption component 112, the head end and the tail end of each of the middle magnetic adsorption component 113 are opposite, and the head end of the first magnetic adsorption component 111 is opposite to the tail end of the second magnetic adsorption component 112.

The primary cleaning mechanism 200 includes primary cleaning components 210. The primary cleaning components 210 can respectively inject a cleaning solution to the reaction cup 20 and extract the waste liquor from the reaction cup 20. A secondary cleaning component 310 can extract the waste liquor from the reaction cup 20. One secondary cleaning component 310 is provided. The secondary cleaning component 310 corresponds to the tail end of the magnetic component (i.e., the second magnetic adsorption component 112) close to the cup outlet station 12, e.g., the secondary cleaning component 310 is located above the tail end of the second magnetic adsorption component 112. For example, three primary cleaning components 210 are provided; the primary cleaning components 210 corresponds to the tail ends of the rest other magnetic adsorption components (the first magnetic adsorption component 111 and the middle magnetic adsorption components 113), e.g., one primary cleaning component 210 is located above the tail end of the first magnetic adsorption component 111 and the other two primary cleaning components 210 are respectively located above the tail ends of the middle magnetic adsorption components 113. The mixing mechanisms 400 correspond to gaps between adjacent (left and right adjacent) two magnetic adsorption components 110. For example, three mixing mechanisms 400 are provided, where one mixing mechanism 400 is located below a gap between the tail end of the first magnetic adsorption component 111 and the head end of the adjacent middle magnetic adsorption component 113, another mixing mechanism 400 is located below a gap between the tail end of one middle magnetic adsorption component 113 and the head end of the other middle magnetic adsorption component 113, and the rest one mixing mechanism 400 is located below a gap between the head end of the second magnetic adsorption component 112 and the tail end of the adjacent middle magnetic adsorption component 113.

The magnetic microbeads adsorption mechanism 100 may further include a pull-down component 114, and the pull-down component 114 is fixed on the mounting circumference of the pedestal 120 and is arranged between the first magnetic adsorption component 111 and the second magnetic adsorption component 112 at an interval along the periphery. A head end of the pull-down component 114 is opposite to the tail end of the second magnetic adsorption component 112, and a tail end of the pull-down component 114 is opposite to the head end of the first magnetic adsorption component 111. In other words, the pull-down component 114 is located on an inferior arc, between the first magnetic adsorption component 111 and the second magnetic adsorption component 112, of the mounting circumference. Therefore, the cup outlet station 12 is arranged close to the head end of the pull-down component 114, and the cup inlet station 11 is arranged close to the tail end of the pull-down component 114. The cleaning device 10 may further include a liquid injection mechanism 500. The liquid injection mechanism 500 is arranged on the pedestal 120. The liquid injection mechanism 500 is configured to inject the cleaning solution to the reaction cup 20 at the cup inlet station 11. When the solution amount in the reaction cup 20 at the cup inlet station 11 is very few and the liquid level is low, it will result in that the magnetic adsorption components 110 cannot form effective adsorption to the magnetic microbeads 30. After the cleaning solution is injected by the liquid injection mechanism 500, the magnetic microbeads 30 may be cleaned on one hand, and on the other hand, the liquid level is increased so that the magnetic microbeads 30 is within a range of a magnetic field of the magnetic adsorption components 110 and the magnetic adsorption components 110 can adsorb the magnetic microbeads 30.

The reaction cup 20 has three movement modes (corresponding to three cleaning modes) along with the turntable 130: ① the reaction cup 20 enters the turntable 130 from the cup inlet station 11 for rotation and sequentially passes through the first magnetic adsorption component 111, the middle magnetic adsorption components 113 and the second magnetic adsorption component 112 to arrive at the cup outlet station 12, i.e., the reaction cup 20 rotates for less than one circumference and arrives at the cup outlet station 12 for a first time; and at this moment, the reaction cup 20 is output from the cup outlet station 12 to a measurement chamber for detection in a next step; ② the reaction cup 20 enters the turntable 130 from the cup inlet station 11 for rotation and sequentially passes through the first magnetic adsorption component 111, the middle magnetic adsorption components 113, the second magnetic adsorption component 112 and the pull-down component 114 to arrive at the cup inlet station 11, i.e., the reaction cup 20 rotates for one circumference and then goes back to the cup inlet station 11; and at this moment, the reaction cup 20 is output from the cup inlet station 11 to a reaction disc to add a sample for a second time; and thereafter, the reaction cup 20 after being added with the sample for the second time enters the cup inlet station 11 again for rotation; and when the reaction cup 20 rotates for less than one circumference and arrives at the cup outlet station 12, the reaction cup 20 is output from the cup outlet station 12 to the measurement chamber for detection in the next step; and ③ the reaction cup 20 enters the turntable 130 from the cup inlet station 11, rotates for several circumferences, and at last, outputs from the cup outlet station 12 to the measurement chamber for detection in the next step.

Referring to FIG. 2 to FIG. 6 simultaneously, the pull-down component 114 and each of the magnetic adsorption components 110 respectively include a support seat 102, a magnetic conductive plate 103 and multiple arc magnets 101. The support seats 102, the magnetic conductive plate 103 and the arc magnets 101 respectively are of a circular arc shape approximately. The support seats 102 are fixed on the mounting circumference of the pedestal 120. The magnetic conductive plates 103 are fixed on surfaces, facing to the reaction cup 20, of the support seats 102, and for example, are fixed via a manner such as bolt connection. The arc magnets 101 are attached to the magnetic conductive plates 103, and for example, are attached via a manner such as glued connection. The multiple arc magnets 101 are arranged on the magnetic conductive plates 103 along the circumferences of the magnetic conductive plates 103. In some embodiments, the pull-down component 114 and each of the magnetic adsorption components 110 are respectively located inside the rotation track of the reaction cup 20, i.e., the mounting circumference is enclosed within the rotation track of the reaction cup 20. In other embodiment, the pull-down component 114 and each of the magnetic adsorption components 110 are also respectively located outside the rotation track of the reaction cup 20.

Specifically, each of the arc magnets 101 includes a first magnet 101a and a second magnet 101b; the polarities of the first magnet 101a and the second magnet 101b are opposite; and the first magnet 101a and the second magnet 101b are overlapped and face to the reaction cup 20. When the reaction cup 20 rotates to lateral sides of the magnetic adsorption components 110 or the pull-down component 114, the magnetic microbeads 30 can be adsorbed to the cup wall of the reaction cup 20 via a magnetic field generated by the arc magnets 101. The magnetic microbeads 30 is provided with an adsorption position on the cup wall of the reaction cup 20, and it is defined that a distance from a geometric center of the adsorption position to a cup bottom of the reaction cup 20 is an adsorption height H of the magnetic microbeads 30. Each of the arc magnets 101 forms a strong magnetic field band with the largest magnetic field intensity, the magnetic microbeads 30 is adsorbed to the reaction cup 30 mainly via a magnetic attraction force of the strong magnetic field band, and it is defined that a distance from the strong magnetic field band to the pedestal 120 is a magnetic adsorption height of each of the arc magnets 101. Generally, since the magnetic field intensity nearby an overlapping position 101c of the first magnet 101a and the second magnet 101b in each of the arc magnets 101 is the largest, the strong magnetic field band is located nearby the overlapping position 101c of the first magnet 101a and the second magnet 101b and thus a distance from the overlapping position 101c to the pedestal 120 is in direct proportion to the magnetic adsorption height. Of course, when the distances from the overlapping positions 101c of the two arc magnets 101 to the pedestal 120 are equal, the magnetic adsorption heights of the two arc magnets 101 are equal. When the magnetic adsorption heights of the arc magnets 101 are larger, under the action of the attractive forces of the strong magnetic field bands, the adsorption height of the magnetic microbeads 30 is also increased, i.e., the magnetic adsorption heights of the arc magnets 101 are in direct proportion to the adsorption height H of the magnetic microbeads 30.

In some embodiments, for the first magnetic adsorption component 111, four arc magnets 101 are provided, and the distance from the overlapping position 101c of each of the arc magnets 101 to the pedestal 120 is equal, i.e., the magnetic adsorption height of each of the arc magnets 101 is equal and is recorded as A. When the reaction cup 20 moves from the head end of the first magnetic adsorption component 111 to the tail end, the adsorption height H of the magnetic microbeads 30 on the reaction cup 20 is unchanged. For the two middle magnetic adsorption components 113, four arc magnets 101 are provided too, and the distance from the overlapping position 101c of each of the arc magnets 101 to the pedestal 120 is equal, i.e., the magnetic adsorption height of each of the arc magnets 101 is equal and is recorded as B, wherein B≥A. When the reaction cup 20 moves from the head ends of the middle magnetic adsorption components 113 to the tail ends, the adsorption height H of the magnetic microbeads 30 on the reaction cup 20 is unchanged. Because of B≥A, the magnetic adsorption height of each of the arc magnets 101 on the middle magnetic adsorption components 113 may be greater than that of each of the arc magnets 101 on the first magnetic adsorption component 111; and for the adsorption height H of the magnetic microbeads 30 on the reaction cup 20, when the reaction cup 20 passes through the middle magnetic adsorption components 113, its value may be greater than that when the reaction cup 20 passes through the first magnetic adsorption component 111. In other words, when the reaction cup 20 rotates from the first magnetic adsorption component 111 to the middle magnetic adsorption components 113, the adsorption height H of the magnetic microbeads 30 on the reaction cup 20 may be increased. In the first magnetic adsorption component 111 and the middle magnetic adsorption components 113, adjacent (left and right adjacent) two arc magnets 101 are abutted against to each other, i.e., no gap is provided therebetween, so that the continuity of the magnetic fields is guaranteed and the magnetic microbeads 30 is prevented from being separated from the cup wall of the reaction cup 20 due to insufficient magnetic attraction forces.

For the second magnetic adsorption component 112, six arc magnets 101 are provided, i.e., the number of the arc magnets 101 is the most relatively. From the head end of the second magnetic adsorption component 112 to the tail end thereof, distances from the overlapping positions 101c of the arc magnets 101 to the pedestal 120 are gradually reduced. When the reaction cup 20 moves from the head end of the second magnetic adsorption component 112 to the tail end, the adsorption height H of the magnetic microbeads 30 on the reaction cup 20 is gradually decreased, so that the adsorption position of the magnetic microbeads 30 on the reaction cup 20 is gradually close to the cup bottom of the reaction cup 20. Specifically, the magnetic adsorption height of the arc magnet 101 closest to the middle magnetic adsorption components 113 on the second magnetic adsorption component 112 is C, wherein the C is equal to the B, i.e., the magnetic adsorption height of the arc magnet 101 located at the head end of the second magnetic adsorption component 112 is equal to the magnetic adsorption heights of the arc magnets 101 on the middle magnetic adsorption components 113. Therefore, in the process when the reaction cup 20 rotates from the cup inlet station 11 to the cup outlet station 12, the adsorption height H of the magnetic microbeads 30 may be increased first and then may be decreased.

In the second magnetic adsorption component 112, two adjacent arc magnets 101 are spaced apart mutually to form a gap therebetween. In order to make up the shortage that a magnetic field is lacked due to no arc magnet 101 at each of the gaps, the second magnetic adsorption component 112 further includes transition magnets 104, and each of the transition magnets 104 is located at the gap between two adjacent arc magnets 101. Owing to the presence of the transition magnets 104, when the reaction cup 20 rotates to the gaps, the transition magnets 104 respectively generate the magnetic field to adsorb the magnetic microbeads 30, and thus the magnetic microbeads 30 is prevented from being separated from the cup wall of the reaction cup 20 to fall into the solution. Identification grooves 103a are further formed on the magnetic conductive plate 103 of the second magnetic adsorption component 112. The identification grooves 103a are approximately located at upper portions of mounting positions of the transition magnets 104. The identification grooves 103a provide the convenience for the installation of the second magnetic adsorption component 112 and take the installation identifying effect.

The structure of the pull-down component 114 is similar to the structure of the second magnetic adsorption component 112, four arc magnets 101 are provided, two adjacent arc magnets 101 are spaced apart mutually to form a gap therebetween, the transition magnets 104 are also arranged in the gaps, and the identification grooves 103a are also formed on the upper portions of the mounting positions of the transition magnets 104. The magnetic adsorption height of the arc magnet 101 located at the head end of the pull-down component 114 is equal to that of the arc magnet 101 at the tail end of the second magnetic adsorption component 112. From the head end of the pull-down component 114 to the tail end thereof, the distances from the overlapping positions 101c of the arc magnets 101 to the pedestal 120 are gradually reduced, i.e., the magnetic adsorption heights of the arc magnets 101 are gradually reduced, so that the adsorption height of the magnetic microbeads 30 on the reaction cup 20 is reduced, and the magnetic microbeads 30 is further close to the cup bottom of the reaction cup 20. When the reaction cup 20 rotates to the tail end of the pull-down component 114, the adsorption height of the magnetic microbeads 30 on this reaction cup 20 is minimum.

Referring to FIG. 2, in some embodiments, an optocoupler 121 is arranged on the pedestal 120, and an induction piece 122 is correspondingly arranged on the turntable 130. When the induction piece 122 moves nearby the optocoupler 121, the optocoupler 121 is excited to generate a level signal, thus taking the effect of defining an initial position of the turntable 130. A cup measurement sensor 124 and a liquid measurement sensor 125 may further be arranged on the pedestal 120. The cup measurement sensor 124 and the liquid measurement sensor 125 both are arranged nearby the cup inlet station 11. The cup measurement sensor 124 is configured to monitor whether a reaction cup 20 is present at the cup inlet station 11 or not, and the liquid measurement sensor 125 is configured to monitor whether the reaction cup 20 located at the cup inlet station 11 has the solution or not.

The magnetic microbeads adsorption mechanism 100 may further includes locating blocks 115 and liquid placement grooves 123. The locating blocks 115 are fixed on the pedestal 120 and are of a circular arc shape approximately. The number of the locating blocks 115 is equal to that (four) of the magnetic adsorption components 110, i.e., one locating block 115 is correspondingly arranged aside the first magnetic adsorption component 111, the middle magnetic adsorption components 113 and the second magnetic adsorption component 112. The locating blocks 115 and the magnetic adsorption components 110 that are corresponding to each other are spaced apart to form a channel for operating the reaction cup 20. With the arrangement of the locating blocks 115, operation track of the reaction cup 20 may be limited, the spaces between the reaction cup 20 and the magnetic adsorption components 110 are reduced, and the adsorption forces of the magnetic adsorption components 110 to the magnetic microbeads 30 in the reaction cup 20 are increased; and thus, the adsorption of the magnetic beads is more complete and the loss is reduced. The liquid placement grooves 123 are formed on the pedestal 120. Four liquid placement grooves 123 may be provided. Each of the liquid placement grooves 123 may be respectively located below the primary cleaning components 210 and the liquid injection mechanism 500; and the liquid placement grooves 123 may catch liquid sprayed out from the primary cleaning component 210 or the liquid injection mechanism 500 in breakdown.

Figure 10:
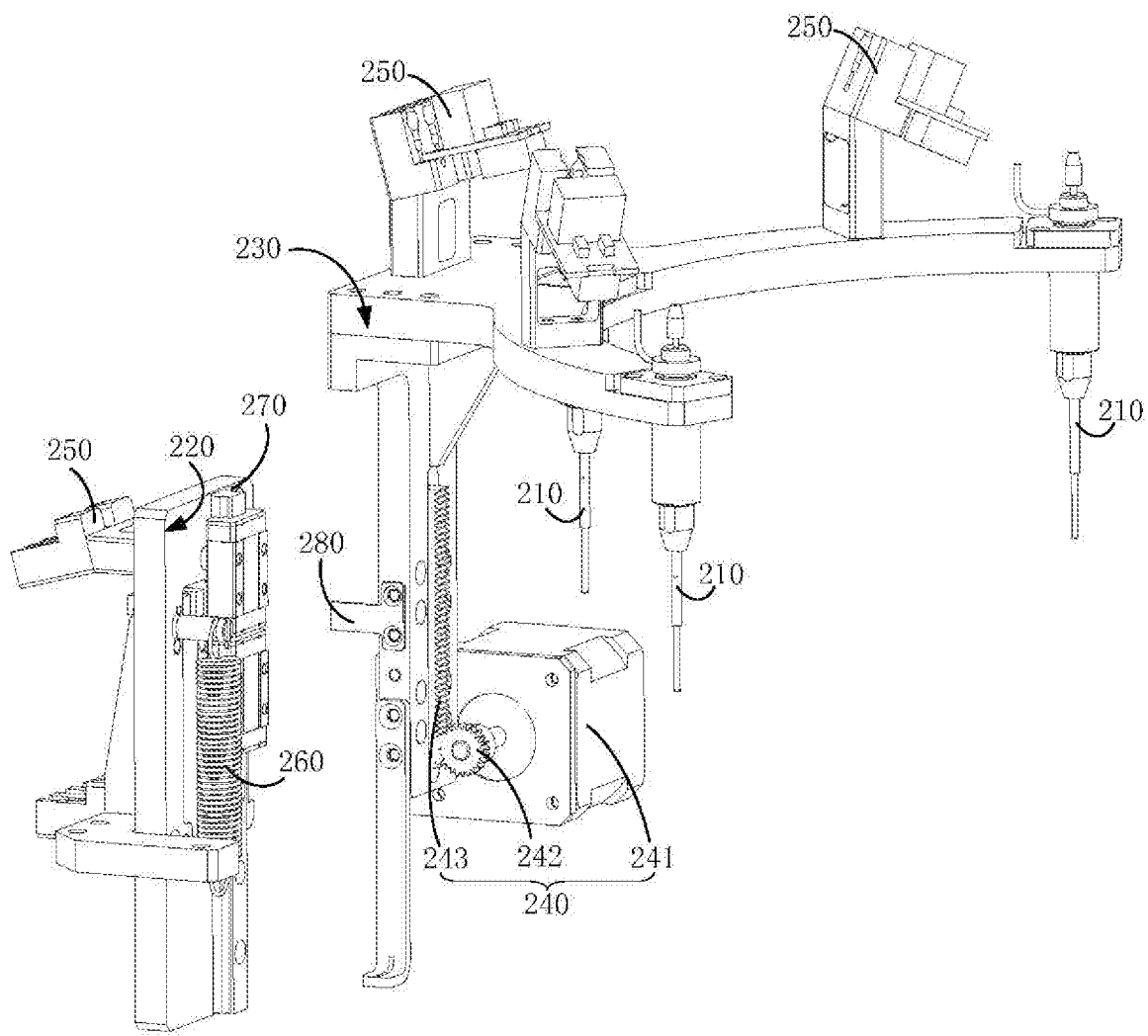
FIG. 10 is an exploded diagram of a primary cleaning mechanism in FIG. 1.
Figure 11:
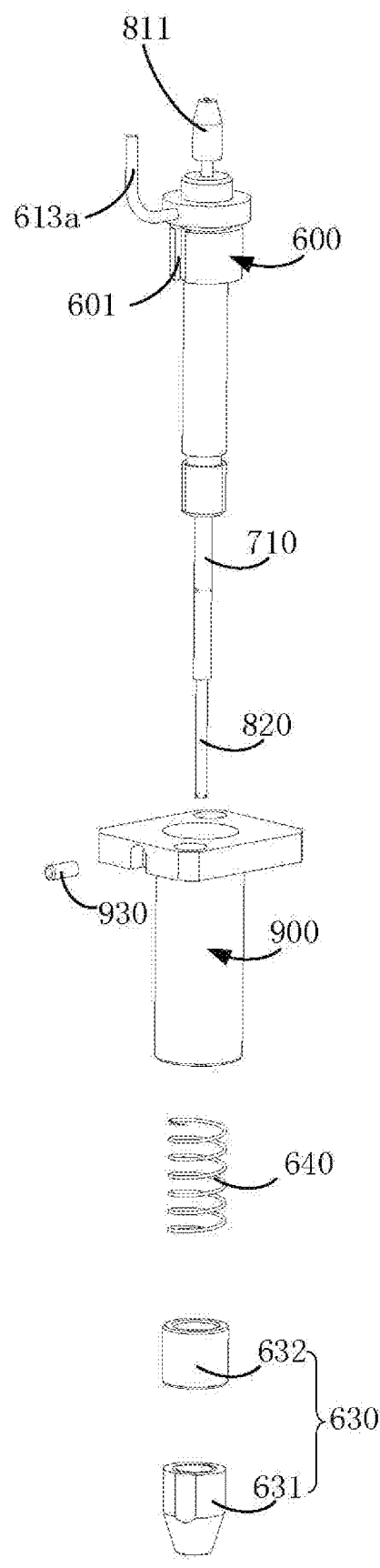
FIG. 11 is an exploded diagram of a primary cleaning mechanism in FIG. 10.
Figure 12:
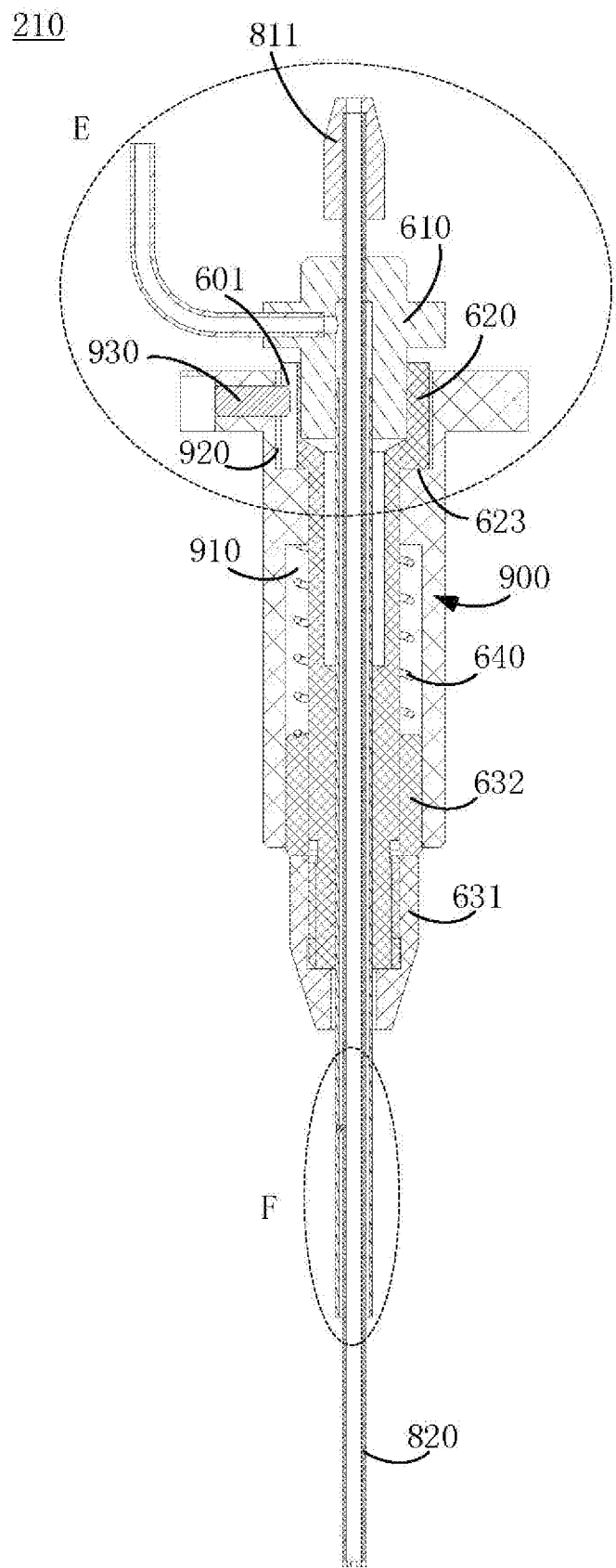
FIG. 12 is a sectional view of a primary cleaning mechanism in FIG. 10.
Figure 13:
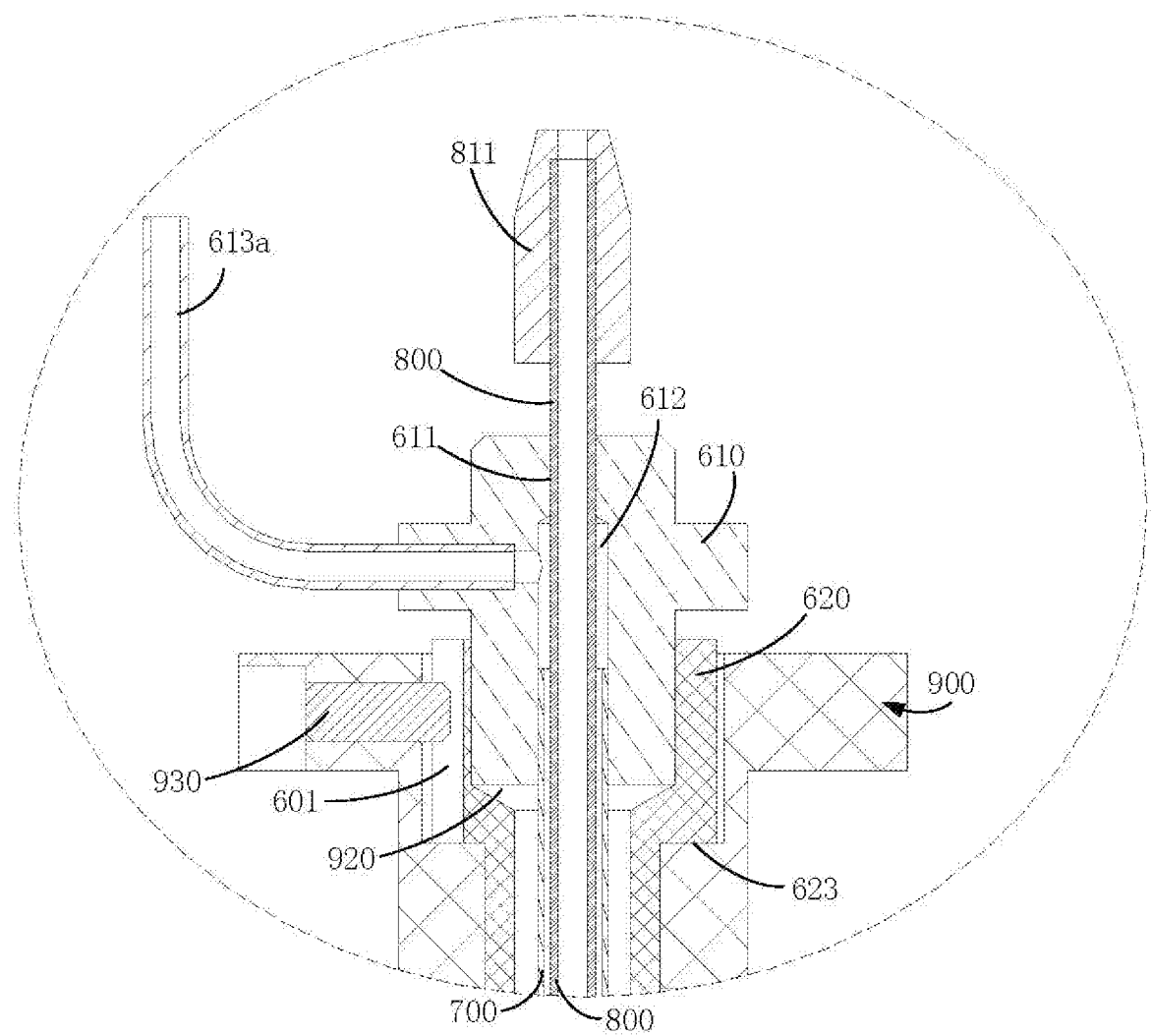
FIG. 13 is a schematic diagram of an enlarged structure of an E place in FIG. 12.
Figure 14:
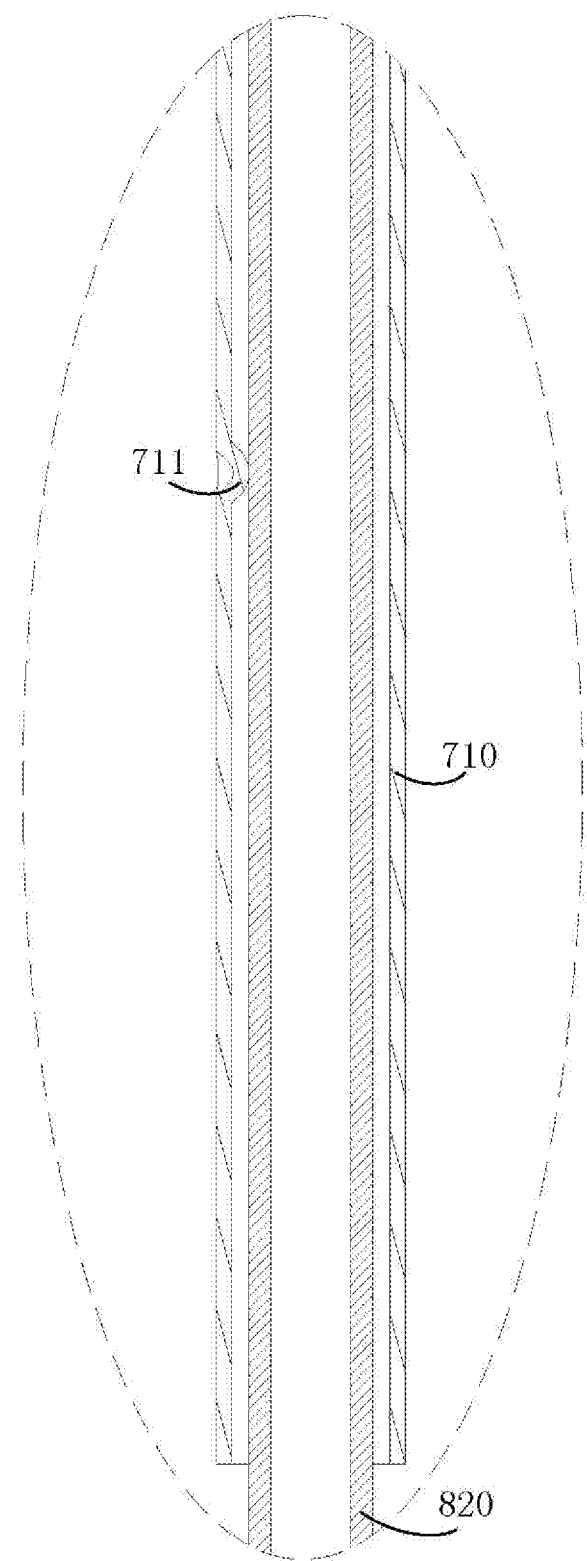
FIG. 14 is a schematic diagram of an enlarged structure of an F place in FIG. 12.
Figure 15:
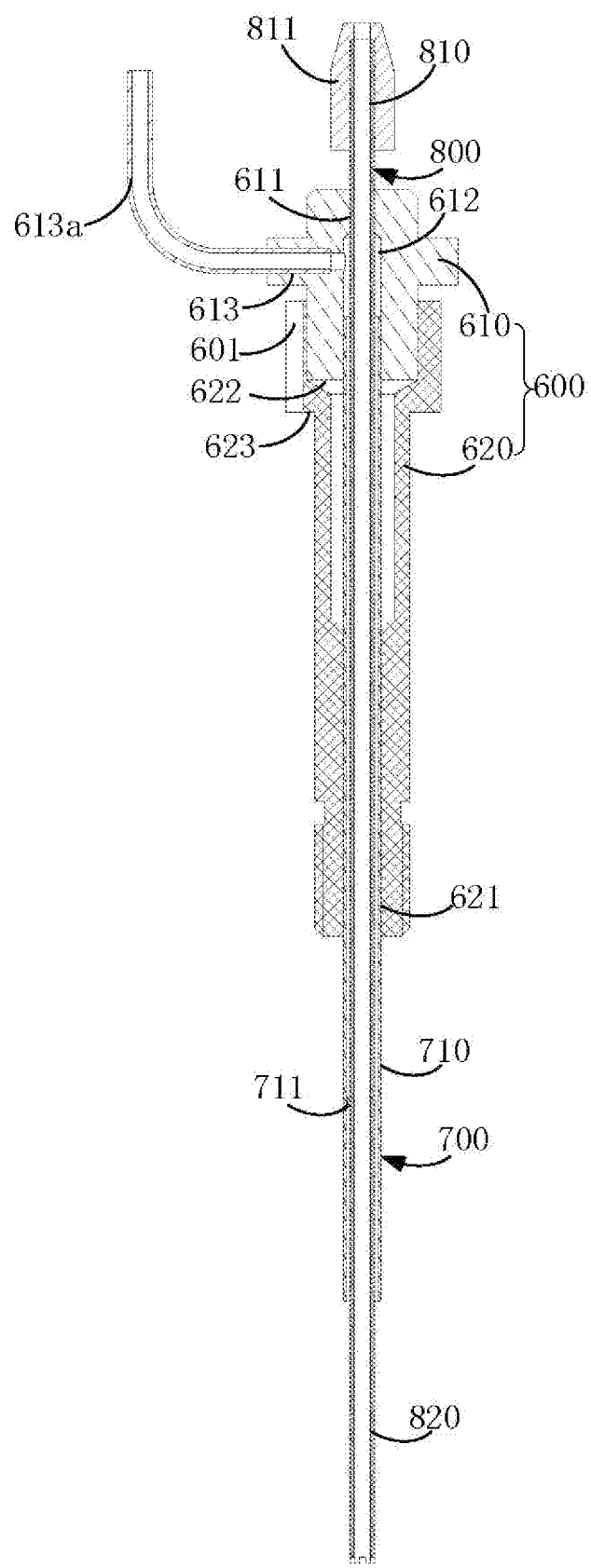
FIG. 15 is a schematic diagram of a local structure of FIG. 12.

Referring to FIG. 1 and FIG. 10, the primary cleaning mechanism 200 further includes a first mounting frame 220, a first support frame 230, a first drive component 240 and pipe clamps 250. The first mounting frame 220 is fixed on the pedestal 120. The first support frame 230 is in a sliding fit with the first mounting frame 220, for example, a linear guide rail is arranged on the first mounting frame 220, the linear guide rail extends along a vertical direction, and a guide groove matched with the linear guide rail is formed on the first support frame 230. The first drive component 240 is connected with the first mounting frame 220, and the first drive component 240 drives the first support frame 230 to slide up and down along the linear guide rail. Multiple pipe clamps 250 may be provided. The pipe clamps 250 are mounted on the first mounting frame 220 and the first support frame 230 and are configured to support liquid injection pipes 613a and the liquid extraction pipes. Three primary cleaning components 210 are mounted on the first support frame 230 at intervals.

The first drive component 240 includes a first motor 241, a gear 242 and a rack 243. The first motor 241 is fixed on the first mounting frame 220. The gear 242 is connected with an output shaft of the first motor 241. The rack 243 is fixed on the first support frame 230 and is meshed with the gear 242. Through the meshed action of the gear 242 and the rack 243, when the first motor 241 is rotated forwardly or reversely, the first support frame 230 may be driven to slide up and down along the linear guide rail relative to the pedestal 120, and thus the primary cleaning components 210 are driven to be close to or far away from the reaction cup 20.

In some embodiment, the primary cleaning mechanism 200 may further includes a first tensile spring 260, limit bolts 270, a first optocoupler and a first baffle piece 280, etc. One end of the first tensile spring 260 is fixed on the first mounting frame 220, and the other end of the first tensile spring 260 is connected with a bottom end of the first support frame 230. When the first motor 241 drives the primary cleaning components 210 to move downwardly to be close to the reaction cup 20, the first tensile spring 260 is in a stretched state. When the first motor 241 cannot normally work due to factors such as sudden power failure, a pull force is generated by the first tensile spring 260 and the first support frame 230 is prevented from driving the primary cleaning components 210 to slide downward, so that the primary cleaning components 210 are prevented from colliding with the reaction cup 20 to damage.

The limit bolts 270 may be arranged at upper and lower ends of the linear guide rail of the first mounting frame 220. The limit bolts 270 can be abutted against the first support frame 230, thus taking the effect of limiting a sliding stroke of the first support frame 230. The first optocoupler is fixed on the first mounting frame 220. The first optocoupler is corresponding to an initial position of the first support frame 230. The first baffle piece 280 is fixed on the first support frame 230. When the first baffle piece 280 moves to the first optocoupler, the first optocoupler is excited to generate the level signal, thus taking the effect of detecting and determining an initial position of the primary cleaning mechanism 200.

Referring to FIG. 11 to FIG. 15 simultaneously, each of the primary cleaning components 210 includes a needle sleeve 600, a liquid injection needle 700 and a liquid extraction needle 800; the needle sleeve 600 is arranged on the first support frame 230; the liquid injection needle 700 sleeves the needle sleeve 600 and is fixedly connected with the needle sleeve 600; the liquid injection needle 700 is configured to inject the cleaning solution to the reaction cup 20; the liquid extraction needle 800 is arranged in the liquid injection needle 700 and the needle sleeve 600 simultaneously in a penetration manner; the liquid extraction needle 800 is fixedly connected with the needle sleeve 600; and the liquid extraction needle 800 is configured to extract waste liquor from the reaction cup 20.

In some embodiment, each of the needle sleeves 600 includes a first sleeve 610 and a second sleeve 620; the first sleeve 610 and the second sleeve 620 may be coaxially arranged and are fixedly connected; a first mounting hole 611 and a second mounting hole 612 are formed in the first sleeve 610; the first mounting hole 611 and the second mounting hole 612 extend axially along the first sleeve 610; a third mounting hole 621 is formed in the second sleeve 620; the third mounting hole 621 extended axially along the second sleeve 620; the first mounting hole 611, the second mounting hole 612 and the third mounting hole 621 are coaxially formed and communicate one another; the first mounting hole 611, the second mounting hole 612 and the third mounting hole 621 are arranged up and down sequentially along the whole needle sleeve 600, i.e., the second mounting hole 612 is formed between the first mounting hole 611 and the third mounting hole 621.

An upper section of the liquid injection needle 700 is matched with a lower portion of the second mounting hole 612. A reserved space is provided between a top end of the liquid injection needle 700 and a bottom wall of the second mounting hole 612, so that the cleaning solution is injected into the liquid injection needle 700 via the reserved space. The upper section of the liquid injection needle 700 may be fixed in the second mounting hole 612 via a welding manner. A middle section of the liquid injection needle 700 is matched with the third mounting hole 621; and the middle section of the liquid injection needle 700 may be fixed in the third mounting hole 621 via a welding manner. Since the upper section and the middle section of the liquid injection needle 700 are fixed, with reference to a principle that a straight line is determined by two points, the liquid injection needle 700 is accurately located and does not swing relative to the needle sleeve 600. A lower section of the liquid injection needle 700 is penetrated through the third mounting hole 621. The lower section of the liquid injection needle 700 is a locating end 710 of the liquid injection needle 700.

A part of the upper section of the liquid extraction needle 800 is matched with the first mounting hole 611; and the liquid extraction needle 800 may be fixed in the first mounting hole 611 via a welding manner. Another part of the upper section of the liquid extraction needle 800 is stretched out of the first mounting hole 611. The part stretched out of the first mounting hole 611 is a connecting end 810 of the liquid extraction needle 800. A needle connecting pipe head 811 is arranged on the connecting end 810, and the needle connecting pipe head 811 is configured to be connected with the liquid extraction pipe. A middle section of the liquid extraction needle 800 is arranged in the second mounting hole 612 and the liquid injection hole 700 in a penetration manner. Centering bumps 711 are arranged on an inner wall surface of the locating end 710 of the liquid injection needle 700. The centering bumps 711 are protruded toward a direction of a central axis of the liquid injection needle 700. Three or four centering bumps 711 may be provided. The centering bumps 711 may be arranged on a same circumference of the inner wall surface of the locating end 710 at intervals. The centering bumps 711 can be abutted against the liquid extraction needle 800 on different radial directions of the circumference, thus taking the locating effect to the liquid extraction needle 800. Since the upper section of the liquid extraction needle 800 is fixed on the first sleeve 610, the middle section of the liquid extraction needle 800 is defined by the centering bumps 711, and simultaneously, the liquid injection needle 700 is located without swing, with reference to the principle that one straight line is determined by two points, the liquid extraction needle 800 is accurately located and does not swing. A lower section of the liquid extraction needle 800 is stretched out of the liquid injection needle 700, and the part stretched out of the liquid injection needle 700 is a liquid extraction end 820 of the liquid extraction needle 800. When the liquid extraction needle 800 extracts the waste liquor in the reaction cup 20, the liquid extraction end 820 is inserted into the solution of the reaction cup 20, and a bottom opening of the liquid extraction end 820 is close to the cup bottom of the reaction cup 20; and thus, the liquid extraction end 820 extracts the waste liquor in the reaction cup 20 completely.

Since the liquid extraction needle 800 is arranged in the liquid injection needle 700 in a penetration manner, after the liquid extraction needle 800 extracts the waste liquor completely, the liquid injection needle 700 starts to inject the cleaning solution to the reaction cup 20, the cleaning solution flowed out from the liquid injection needle 700 is flowed into the reaction cup 20 along the outer wall surface of the liquid extraction end 820, and the downstream cleaning solution cleans residual waste liquor attached on the outer wall surface of the liquid extraction end 820. In a process when the liquid extraction needle 800 extracts the solution again, the residual waste liquor attached on the outer wall surface of the liquid extraction end 820 may be effectively prevented from entering the solution of a next reaction cup 20 and thus the cross contamination is prevented. Meanwhile, the liquid extraction needle 800 arranged in the liquid injection needle 700 in a penetration manner does not occupy an additional space. As long as the liquid injection needle 700 can be inserted into the reaction cup 20, the liquid injection needle 700 and the liquid extraction needle 800 can be inserted into the reaction cup 20 simultaneously, so that the whole primary cleaning component 210 is compact in structure, the caliber of the reaction cup 20 may also be reduced as much as possible and the size of the cleaning device 10 is further reduced. Furthermore, bubbles generated in the process when the liquid injection needle 700 injects the cleaning solution may also be reduced.

More importantly, the centering bumps 711 on the liquid injection needle 700 take the very good locating effect on the liquid extraction needle 800, so when the liquid extraction needle 800 is inserted into the reaction cup 20, the liquid extraction needle 800 does not swing relative to the reaction cup 20 and the position of the liquid extraction needle 800 is determined relative to the reaction cup 20. In this way, the liquid extraction needle 800 may be prevented from swinging to the vicinity of the adsorption position of the magnetic microbeads 30 to extract the magnetic microbeads 30 away, and the loss of the magnetic microbeads 30 is prevented from affecting a subsequent detection result.

A communication hole 613 is further formed on the first sleeve 610, the communication hole 613 communicates with the second mounting hole 612 and the communication hole 613 is configured to mount each of the liquid injection pipe 613a. During the process when the cleaning solution is injected, the cleaning solution in the liquid injection pipe 613a flows through the second mounting hole 612, enters a circulation space enclosed between the liquid injection needle 700 and the liquid extraction needle 800, and at last flows into the reaction cup 20 along the liquid extraction end 820 of the liquid extraction needle 800.

An accommodation cavity 622 is further formed on the second sleeve 620; the accommodation cavity 622 communicates with the third mounting hole 621; the cross-sectional size of the accommodation cavity 622 is greater than that of the third mounting hole 621, and the first sleeve 610 is inserted into and fixed in the accommodation cavity 622. As a matter of fact, the accommodation cavity 622 takes the locating effect to the installation of the first sleeve 610, and the first sleeve 610 may be fixed in the accommodation cavity 622 via a welding manner.

In some embodiments, each of the primary cleaning components further includes a needle holder 900, a spring 640 and a abutting piece 630. The needle holder 900 is fixed on the first support frame 230, and the needle sleeve 600 sleeves in the needle holder 900. Specifically, an outer wall surface of the second sleeve 620 of the needle sleeve 600 is sunken to form a sliding groove 601. The sliding groove 601 extends axially along the second sleeve 620. A guide post 930 is mounted on the needle holder 900. The guide post 930 is in a sliding fit with the sliding groove 601. Therefore, the needle sleeve 600 may be slid up and down relative to the needle holder 900. And meanwhile, through the cooperation of the guide post 930 and the sliding groove 601, the rotation of the needle sleeve 600 relative to the needle holder 900 may be limited.

The abutting piece 630 is arranged on a lower end portion of the needle sleeve 600. A first step hole 910 is formed in the needle holder 900. The needle sleeve 600 is arranged in the first step hole 910 in a penetration manner. The spring 640 sleeves the needle sleeve 600 and can be held in the first step hole 910. The spring 640 is abutted against between a bottom wall of the first step hole 910 and the abutting piece 630. When the needle sleeve 600 is slid upward relative to the needle holder 900, the propping piece 630 can compress the spring 640.

By arranging the spring 640 and sleeving the needle sleeve 600 in the needle holder 900, when the liquid extraction needle 800 is collided with the cup bottom of the reaction cup 20 in breakdown, the liquid extraction needle 800 drives the needle sleeve 600 to slide upward relative to the needle holder 900, the needle sleeve 600 squeezes the spring 640 and the spring 640 is shrunk to absorb impact energy on the liquid extraction needle 800; and thus, the damage to the liquid extraction needle 800 and the reaction cup 20 is prevented. And meanwhile, under the action of a pushing force of the spring 640, the liquid extraction needle 800 can contact the cup bottom of the reaction cup 20 and thus it is assured that the waste liquor in the reaction cup 20 can be completely adsorbed by the liquid extraction needle 800. After the breakdown is removed, the spring 640 pushes the needle sleeve 600 to move downward to reset.

In some embodiments, each of the abutting pieces 630 includes a fixed sleeve 631 and a slidable sleeve 632; the fixed sleeve 631 and the slidable sleeve 632 are arranged in a split manner; the fixed sleeve 631 may be fixed on a lower end of the needle sleeve 600 via a threaded connection manner; the slidable sleeve 632 sleeves the needle sleeve 600 and is in a sliding fit with the first step hole 910; one end of the slidable sleeve 632 is abutted against the fixed sleeve 631, and the other end of the slidable sleeve 632 is abutted against the spring 640; and when the needle sleeve 600 is slid upward relative to the needle holder 900, the fixed sleeve 631 can push the slidable sleeve 632 to compress the spring 640.

In some embodiment, a second step hole 920 is formed on the needle holder 900; an outer wall surface of the needle sleeve 600 is protruded outward along a radial direction and extends to form a lug boss 623; the lug boss 623 can be abutted against a bottom wall of the second step hole 920; and through the abutting effect of the lug boss 623, the location of the needle sleeve 600 relative to the needle holder 900 may be implemented. For example, the lug boss 623 may be arranged on the second sleeve 620 of the needle sleeve 600.

Figure 16:
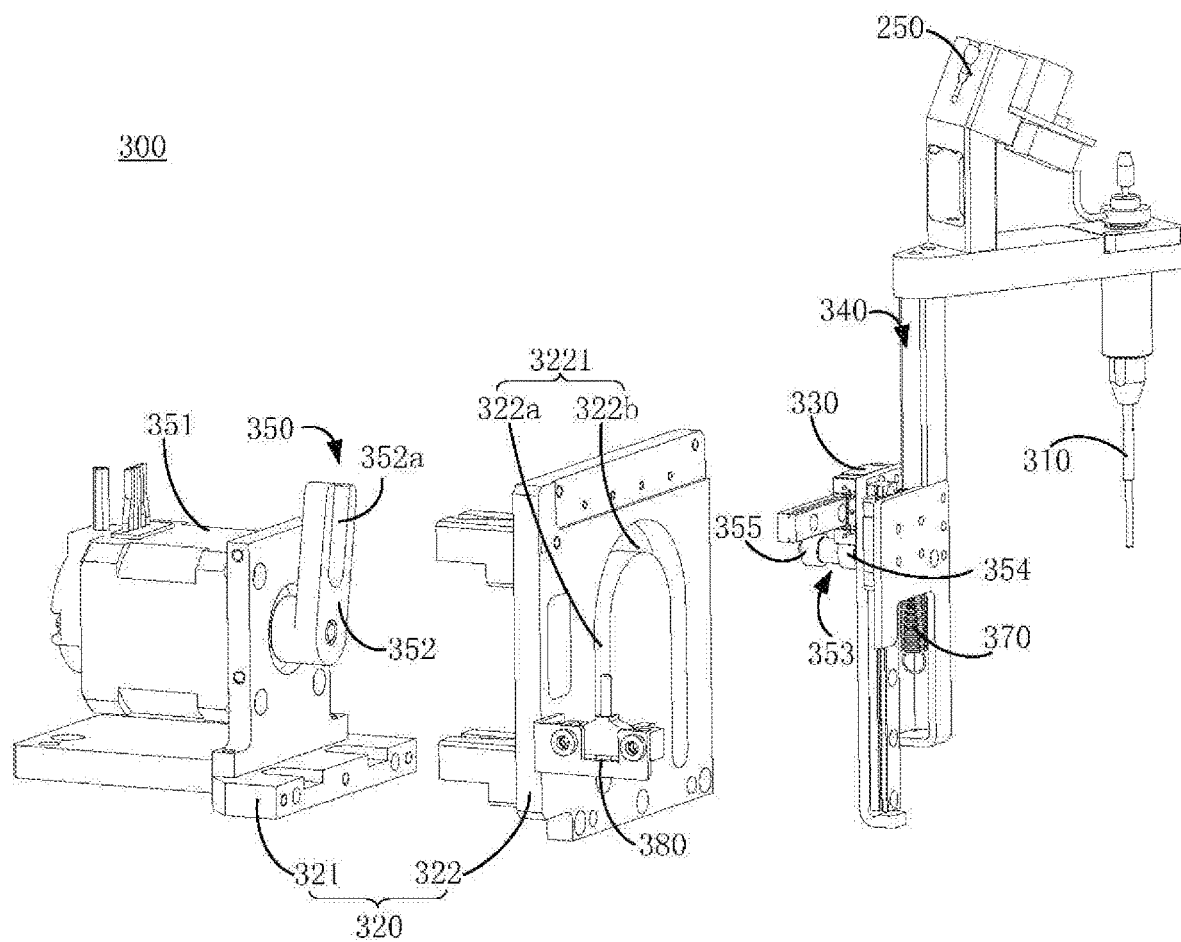
FIG. 16 is an exploded diagram of a secondary cleaning mechanism in FIG. 1.

Referring to FIG. 1 and FIG. 16, the secondary cleaning mechanism 300 further includes a second mounting frame 320, a second support frame 340, a second drive component 350, a slide block 330, a cleaning groove 360 and pipe clamps 250; the second mounting frame 320 includes a first fixed plate 321 and a second fixed plate 322 that are spaced apart; the first fixed plate 321 and the second fixed plate 322 both are fixedly connected with the pedestal 120; a U-shaped groove 3221 is formed on the second fixed plate 322; and an opening of the U-shaped groove 3221 is provided toward the pedestal 120, in other words, the U-shaped groove 3221 is an inverted U-shaped groove 3221. Specifically, the U-shaped groove 3221 includes a circular arc groove section 322b and linear groove sections 322a; the circular arc groove section 322b may be a semi-circular arc groove section 322b; the linear groove sections 322a extends along a vertical direction and two linear groove sections 322a are provided; the two linear groove sections 322a are spaced apart on a horizontal direction; the two linear groove sections 322a both communicate with the circular arc groove section 322b; sidewalls of the linear groove sections 322a are in a tangent relationship with a sidewall of the circular arc groove section 322b; and the circular arc groove section 322b is located above the linear groove sections 322a and is bent toward the pedestal 120.

Multiple pipe clamps 250 may be provided and are fixed on the second fixed plate 322 and the second support frame 340. The pipe clamps 250 are configured to support the liquid extraction pipes. The secondary cleaning component 310 is arranged on the second support frame 340. The secondary cleaning component 310 includes the liquid extraction needle 800 and may not be provided with the liquid injection needle 700. In other words, the secondary cleaning component 310 is the primary cleaning component 210 without the liquid injection needle 700, i.e., by removing the liquid injection needle 700 on the primary cleaning component 210, the secondary cleaning component 310 may be formed. It is easily understood that, in other embodiments, the liquid injection needle 700 on the primary cleaning component 210 may also not be removed to directly form the secondary cleaning component 310 as long as a liquid injection operation is not carried out.

The slide block 330 may be arranged on the second fixed plate 332 of the second mounting frame 320. For example, a linear guide rail extending along a horizontal direction may be arranged on the second fixed plate 332, a guide groove is formed on the slide block 330, and through a sliding fit between the linear guide rail and the guide groove, the slip of the slide block 330 relative to the second mounting frame 320 in the horizontal direction may be implemented. The second support frame 340 is in a sliding fit with the slide block 330 in the vertical direction. For example, a linear guide rail extending along the vertical direction is mounted on the slide block 330, i.e., the linear guide rail is perpendicular to the linear guide rail arranged on the second fixed plate 322; a guide groove is formed on the second support frame 340; and through a sliding fit between the linear guide rail and the guide groove, the slip of the second support frame 340 relative to the slide block 330 in the vertical direction may also be implemented. Therefore, by virtue of the slip of the slide block 330 in the horizontal direction and the slip of the second support frame 340 relative to the slide block 330 in the vertical direction, it may be implemented that the secondary cleaning component 310 moves along with the second support frame 340 in the horizontal direction and the vertical direction.

The second drive component 350 is connected with the second mounting frame 320, and the second drive component 350 is configured to drive the second support frame 340 to slide relative to the second mounting frame 320 in the horizontal direction and the vertical direction. Specifically, the second drive component 350 includes a second motor 351, a rotary block 352 and a guide rod 353; the rotary block 352 is fixed on an output shaft of the second motor 351; a clamping groove 352a is formed on the rotary block 352; and the clamping groove 352a may be a linear strip groove. The guide rod 353 is fixed on the second support frame 340, and the guide rod 353 is simultaneously arranged in the clamping groove 352a and the U-shaped groove 3221 in a penetration manner; and when the second motor 351 drives the rotary block 352 to rotate, the rotary block 352 drives the guide rod 353 to move along a track defined by the U-shaped groove 3221 and thus it is implemented that the secondary cleaning component 310 moves along with the second support frame 340 relative to the second mounting frame 320 in the horizontal direction and the vertical direction.

When the second motor 351 rotates forwardly, the rotary block 352 drives the guide rod 353 to move downward along one linear groove section 322a on the U-shaped groove 3221, the guide rod 353 drives the second support frame 340 to move downward, and further the liquid extraction needle 800 on the secondary cleaning component 310 moves downward and extends into the reaction cup 20 to perform waste liquor extraction treatment. When the waste liquor in the reaction cup 20 is extracted completely, the second motor 351 rotates reversely, the rotary block 352 drives the guide rod 353 to move upward along one linear groove section 322a on the U-shaped groove 3221, the guide rod 353 drives the second support frame 340 to move upward, and further the liquid extraction needle 800 on the secondary cleaning component 310 moves upward and is far away from the reaction cup 20. In a case where the second motor 351 still rotates reversely, the guide rod 353 moves along the circular arc groove section 322b on the U-shaped groove 3221; at this moment, under the action of the guide rod 353, the slide block 330 is slid relative to the second fixed plate 322 in the horizontal direction, and meanwhile, the second support frame 340 is slid up and down relative to the slide block 330; and in a case where the second motor 351 continues to rotate reversely, the guide rod 353 moves downward along the other linear groove section 322a on the U-shaped groove 3221, the secondary cleaning component 310 moves downward along with the second support frame 340 and further the liquid extraction needle 800 is stretched into the cleaning groove 360 for cleaning to prevent the cross contamination. Therefore, when the second motor 351 is circulated to rotate forwardly and reversely, the liquid extraction needle of the secondary cleaning component 310 may be driven to circularly move between the reaction cup 20 and the cleaning groove 360, thereby implementing the waste liquor extraction function of the liquid extraction needle 800 to the reaction cup 20 and the cleaning function of the cleaning groove 360 to the liquid extraction needle 800.

In some embodiments, the second drive component 350 further includes a first rolling element 354 and a second rolling element 355. For example, a bearing may be adopted by the first rolling element 354 and the second rolling element 355 respectively. The first rolling element 354 and the second rolling element 355 are spaced apart on the guide rod 353. The first rolling element 354 is matched with the U-shaped groove 3221. The second rolling element 355 is matched with the clamping groove 352a. Since a friction force of the first rolling element 354 and the second rolling element 355 during movement is a rolling friction force, the movement resistance of the guide rod 353 during the movement may be effectively reduced, and the flexibility of the movement of the whole secondary cleaning mechanism 300 is improved.

In some embodiments, the secondary cleaning mechanism 300 may further include a second tensile spring 370, a second optocoupler 380 and a second baffle piece, etc. One end of the second tensile spring 370 is fixed on the second mounting frame 322 of the second mounting frame 320, and the other end of the second tensile spring 370 is connected with a bottom end of the second support frame 340. When the second motor 351 drives the secondary cleaning components 310 to move downwardly to be close to the reaction cup 20, the second tensile spring 370 is in a stretched state. When the second motor 351 cannot normally work due to factors such as sudden power failure, a pull force is generated by the second tensile spring 370 and the second support frame 340 is prevented from driving the secondary cleaning component 310 to slide downward under the action of the gravity, so that the secondary cleaning component 310 is prevented from colliding with the reaction cup 20 to damage. The second optocoupler 380 is fixed on the second mounting frame 322 of the second mounting frame 320. The second optocoupler 380 is corresponding to an initial position of the second support frame 340. The second baffle piece is fixed on the second support frame 340. When the second baffle piece moves to the second optocoupler 380, the second optocoupler 380 is excited to generate the level signal, thus taking the effect of detecting and determining an initial position of the secondary cleaning mechanism 300.

Figure 17:
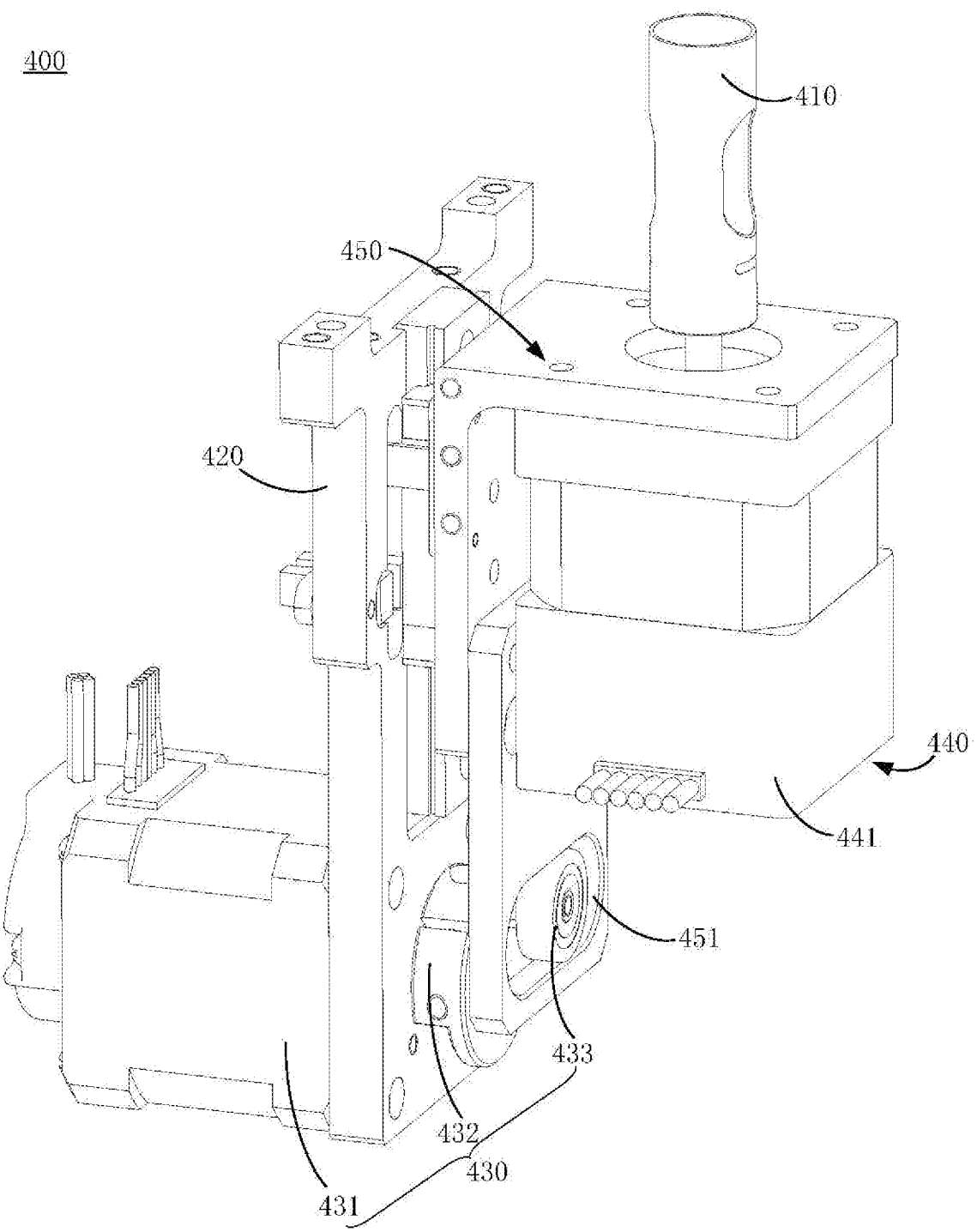
FIG. 17 is a stereoscopic diagram of a mixing mechanism in FIG. 1.

Referring to FIG. 1 and FIG. 17 simultaneously, each of the mixing mechanism 400 includes a third mounting frame 420, a third support frame 450, a third drive component 430, a fourth drive component 440 and a mixing rotor 410. The third mounting frame 420 is fixed on the pedestal 120. The third support frame 450 is slidably arranged on the third mounting frame 420. For example, a linear guide rail extending along the vertical direction is arranged on the third mounting frame 420, a guide groove is formed on the third support frame 450, and through a sliding fit between the linear guide rail and the guide groove, it may be implemented that the third support frame 450 is slid up and down relative to the third mounting frame 420. The third drive component 430 is connected with the third mounting frame 420 and can drive the third support frame 450 to slide. The fourth drive component 440 is arranged on the third support frame 450. The mixing rotor 410 is eccentrically arranged on the fourth drive component 440. The fourth drive component 440 may be a fourth motor 441. For example, the mixing rotor 410 is an opened cylinder, the reaction cup 20 may be held in the opened cylinder, and a bottom wall of the opened cylinder is eccentrically connected to an output shaft of the fourth drive component 440; and when the fourth motor 441 works, because of the eccentricity, the mixing rotor 410 is vibrated and then the vibrated mixing rotor 410 can uniformly mix a suspension liquid in the reaction cup 20. An internal chamfering may be provided at an opening of the mixing rotor 410, so that the reaction cup 20 enters smoothly and is held in the mixing rotor 410.

The third drive component 430 includes a third motor 431, a rotary seat 432 and a third rolling element 433. The third motor 431 is mounted on the third mounting frame 420. The rotary seat 432 is connected with an output shaft of the third motor 431. The rotary seat 432 may be of a disc shape. A center of the disc shape is connected with the output shaft of the third motor 431. The third rolling element 433 may be a bearing. The third rolling element 433 is eccentrically arranged on the rotary seat 432, i.e., a set distance is kept between a mounting position of the third rolling element 433 on the rotary seat 432 and a center of the rotary seat 432. A rolling groove 451 is formed on the third support frame 450. The third rolling element 433 is matched with the rolling groove 451. When the third motor 431 drives the rotary seat 432 to rotate, the third rolling element 433 moves along a track defined by the rolling groove 451 and pushes the third support frame 450 to slide up and down. As a matter of fact, the third drive component 430 may be equivalent to a cam mechanism, the rotary seat 432 provided with the third rolling element 433 is a cam, and the third support frame 450 provided with the rolling groove 451 is an ejector rod matched with the cam.

Each of the mixing mechanism 400 may further includes an optocoupler and an induction piece. The optocoupler is arranged on the third mounting frame 420. The induction piece is arranged on the third support frame 450. The optocoupler is corresponding to an initial position of the third support frame 450. When the induction piece moves to the optocoupler, the optocoupler is excited to generate the level signal, thus taking the effect of detecting and determining the initial position of the mixing rotor 410.

When the cleaning device 10 works, an early preparation step is performed first: incubated reaction cup 20 is placed into the turntable 130 from the cup inlet station 11 via a manipulator; according to a demand in an actual condition, for example, when liquid level in the reaction cup 20 is low, the liquid injection mechanism 500 may inject a cleaning solution to the reaction cup 20 at the cup inlet station 11, and in the process when the cleaning solution is injected, the cleaning solution scours and cleans the magnetic microbeads 30. At this moment, the liquid level in the reaction cup 20 is relatively low.

First step, the turntable 130 rotates continuously; the reaction cup 20 rotates from the head end of the first magnetic adsorption component 111 to the tail end; under the action of the magnetic field of the arc magnets 101 on the first magnetic adsorption component 111, the magnetic microbeads 30 suspended in the cleaning solution is gradually close till it is completely adsorbed to the cup wall of the reaction cup 20; and in the process when the magnetic microbeads 30 moves to the cup wall of the reaction cup 20, the cleaning solution cleans the magnetic microbeads 30. Since the liquid level in the reaction cup 20 is low, in order to effectively adsorb all magnetic microbeads 30, prevent the unadsorbed magnetic microbeads 30 from being extracted away to lost in a subsequent waste liquor extraction process and thus guarantee a detection result, the magnetic adsorption heights (height value is A) of the arc magnets 101 in the first magnetic adsorption component 111 are slightly low and the adsorption height of the magnetic microbeads 30 on the reaction cup 20 is slightly low. When the reaction cup 20 arrives at the tail end of the first magnetic adsorption component 111, the turntable 130 is suspended to rotate. At this moment, under the action of the first drive component 240 on the primary cleaning mechanism 200, the primary cleaning components 210 move downward and the liquid extraction needle 800 is inserted into the reaction cup 20 to extract waste liquor. By adsorbing the magnetic microbeads 30 to the reaction cup 20, the magnetic microbeads 30 is in a gathered state. When the waste liquor is extracted, position of the liquid extraction needle 800 in the reaction cup 20 is adjusted to a side far away from the magnetic microbeads 30, so that the liquid extraction needle 800 keeps far away from the adsorption position of the magnetic microbeads 30; and in this way, the liquid extraction needle 800 may be effectively prevented from extracting a part of the magnetic microbeads 30 to affect the detection result. After the waste liquor is extracted completely, the liquid injection needles 700 of the primary cleaning components 210 inject the cleaning solution, and the cleaning solution is flowed out from gaps between the liquid injection needles 700 and the liquid extraction needle 800 first and then is flowed into the reaction cup 20 along the outer wall surface of the liquid extraction needle 800; the cleaning solution scours the magnetic microbeads 30 to take the cleaning effect; and meanwhile, the cleaning solution cleans the residual waste liquor on the liquid extraction needle 800 so as to prevent the cross contamination; after the cleaning solution is injected into the reaction cup 20, the liquid level in the reaction cup 20 is higher than that at the cup inlet station 11; and after the cleaning solution is injected completely, the first drive component 240 drives the primary cleaning components 210 to move upward, so that the liquid extraction needle 800 is completely far away from the reaction cup 20 for the fear that the rotation of the reaction cup 20 is affected. Next, the reaction cup 20 rotates to gaps between the first magnetic adsorption component 111 and the middle magnetic adsorption components 113 and are suspended. At this moment, the third drive component 430 of the mixing mechanism 400 drives the mixing rotor 410 to move upward and get close to the reaction cup 20, so that the reaction cup 20 is held in the mixing rotor 410; then, the fourth drive component 440 starts to work, the mixing rotor 410 drives the reaction cup 20 to vibrate, and the cleaning solution effectively cleans the magnetic microbeads 30 because of vortex generated by vibration; and after a vibration for a setting time, the fourth drive component 440 stops to work, and the third drive component 430 drives the mixing rotor 410 to move downward to completely separate from the reaction cup 20 for the fear that the rotation of the reaction cup 20 is affected.

Second step, the reaction cup 20 rotates and moves from the head end of one middle magnetic adsorption component 113 to the tail end thereof; under the action of the magnetic field of the arc magnets 101 on the middle magnetic adsorption component 113, the magnetic microbeads 30 suspended in the cleaning solution is gradually close till it is completely adsorbed to the cup wall of the reaction cup 20; and in the process when the magnetic microbeads 30 moves to the cup wall of the reaction cup 20, the cleaning solution cleans the magnetic microbeads 30. Since the liquid level in the reaction cup 20 is relatively high at this moment, in order to effectively adsorb all magnetic microbeads 30, the magnetic adsorption heights (height value is B) of the arc magnets 101 on the middle magnetic adsorption component 113 are slightly higher than the adsorption height (height value is A)

of the first magnetic adsorption component 111, and the adsorption height H of the magnetic microbeads 30 on the reaction cup 20 is slightly higher. When the reaction cup 20 arrives at the tail end of this middle magnetic adsorption component 113, the primary cleaning components 210 inject the cleaning solution and extract the waste liquor in the reaction cup 20, and the working process of each of the primary cleaning components 210 is referred to related corresponding description in the first step. Likewise, When the reaction cup 20 rotates to gaps between the two middle magnetic adsorption components 113, the mixing mechanism 400 uniformly mixes the reaction cup 20, and the working process of the mixing mechanism 400 is also referred to the related corresponding description in the first step.

Third step, the reaction cup 20 rotates and moves from the head end of the other middle magnetic adsorption component 113 to the tail end thereof. Since the structures of the two middle magnetic adsorption components 113 are completely the same, the adsorption process of magnetic beads on the reaction cup 20, and the cleaning solution injection and waste liquor extraction processes of the primary cleaning components 210 all may be referred to the related corresponding description in the first step or the second step. Likewise, when the reaction cup 20 rotates to the gaps between the middle magnetic adsorption components 113 and the second magnetic adsorption component 112, the working process of the mixing mechanism 400 is also referred to the related corresponding description in the first step or the second step.

Fourth step, the reaction cup 20 rotates and moves from the head end of the second magnetic adsorption component 112 to the tail end thereof. Along the rotation direction of the reaction cup 20, the magnetic adsorption heights of the arc magnets 101 on the second magnetic adsorption component 112 are gradually reduced. As a result, when the reaction cup 20 arrives at the tail end of the second magnetic adsorption component 112, the adsorption height H of the magnetic microbeads 30 on the reaction cup 20 is low, the second drive component 350 on the secondary cleaning mechanism 300 works, the secondary cleaning component 310 is driven to move downward to be close to the reaction cup 20, and after extracting the waste liquor completely, the liquid extraction needle 800 of the secondary cleaning component 310 is far away from the reaction cup 20. At this moment, there is no liquid in the reaction cup 20, and the magnetic microbeads 30 is relatively close to the cup bottom of the reaction cup 20. Next, the reaction cup 20 rotates to the cup outlet station 12. Herein, there are two cases: (1) when the detection is required, the reaction cup is conveyed to the measurement chamber via the manipulator for detection. Since the adsorption height of the magnetic microbeads 30 is low, when a set amount of detection reagent is added to the reaction cup 20 in the measurement chamber, the detection reagent may completely soak the magnetic microbeads 30, so that the magnetic microbeads 30 is fully reacted with the detection reagent and thus the accuracy of the detection result is improved. (2) When the secondary sample adding is required, the reaction cup 20 may be enabled to rotate continuously and arrive at the cup inlet station 11 via the pull-down component 114; and then, the reaction cup 20 arriving at the cup inlet station 11 is conveyed to the reaction disc via the manipulator for secondary sample adding. The working process is referred to the following fifth step.

Fifth step, the reaction cup 20 rotates from the head end of the pull-down component 114 to the tail end thereof. Since the magnetic adsorption heights of the arc magnets 101 on the pull-down component 114 are gradually reduced, the magnetic adsorption height of the arc magnet 101 located at the tail end of the pull-down component 114 is smaller than that of other magnetic adsorption components. When the reaction cup 20 arrives at the tail end, the adsorption height of the magnetic microbeads 30 on the reaction cup 20 is minimum and the magnetic microbeads 30 is further close to the cup bottom of the reaction cup 20. When the reaction cup 20 rotates to the cup inlet station 11, the reaction cup 20 arriving at the cup inlet station 11 is conveyed to the reaction disc via the manipulator for secondary sample adding, i.e., a small amount of secondary reagent is added to the reaction cup 20. Since the magnetic microbeads 30 is nearest to the cup bottom of the reaction cup 20, the small amount of secondary agent can also soak the magnetic microbeads 30. After the secondary reagent is added completely, the reaction cup 20 is put into the turntable 130 from the cup inlet station 11 and rotates; and through the cleaning process from the first step to the fourth step, the reaction cup 20 is conveyed to the measurement chamber from the cup outlet station 12 for detection at last.

The reaction cup 20 rotates from the cup inlet station 11, sequentially passes through the first magnetic adsorption component 111 and the middle magnetic adsorption components 113 to arrive at the gap between the middle magnetic adsorption components 113 and the second magnetic adsorption component 112 and are vibrated by the mixing mechanism 400. The whole process is corresponding to the cleaning process from the first step to the third step and this cleaning process relates to the participation of the primary cleaning components 210. Therefore, the cleaning process from the first step to the third step may be defined as the primary cleaning. The reaction cup 20 moves from the head end of the second magnetic adsorption component 112 to the tail end thereof and the waste liquor is extracted. The whole process is corresponding to the cleaning process in the fourth step and this process relates to the participation of the secondary cleaning component 310. Therefore, the cleaning process in the fourth step may be defined as the secondary cleaning.

In order to clean the magnetic microbeads 30 more completely, the reaction cup 20 may rotate for multiple circles, i.e., after multiple rounds of the primary cleaning and the secondary cleaning, the reaction cup 20 is conveyed to the measurement chamber from the cup outlet station 12 for detection.

The present disclosure further provides a chemiluminescence detector, which includes the above-mentioned cleaning device 10.

The present disclosure further provides a cleaning method. A predetermined cleaning working mode is selected according to a type of a reagent loaded to reaction cup. The cleaning method includes a first working mode, a second working mode and a third working mode.

Figure 18:
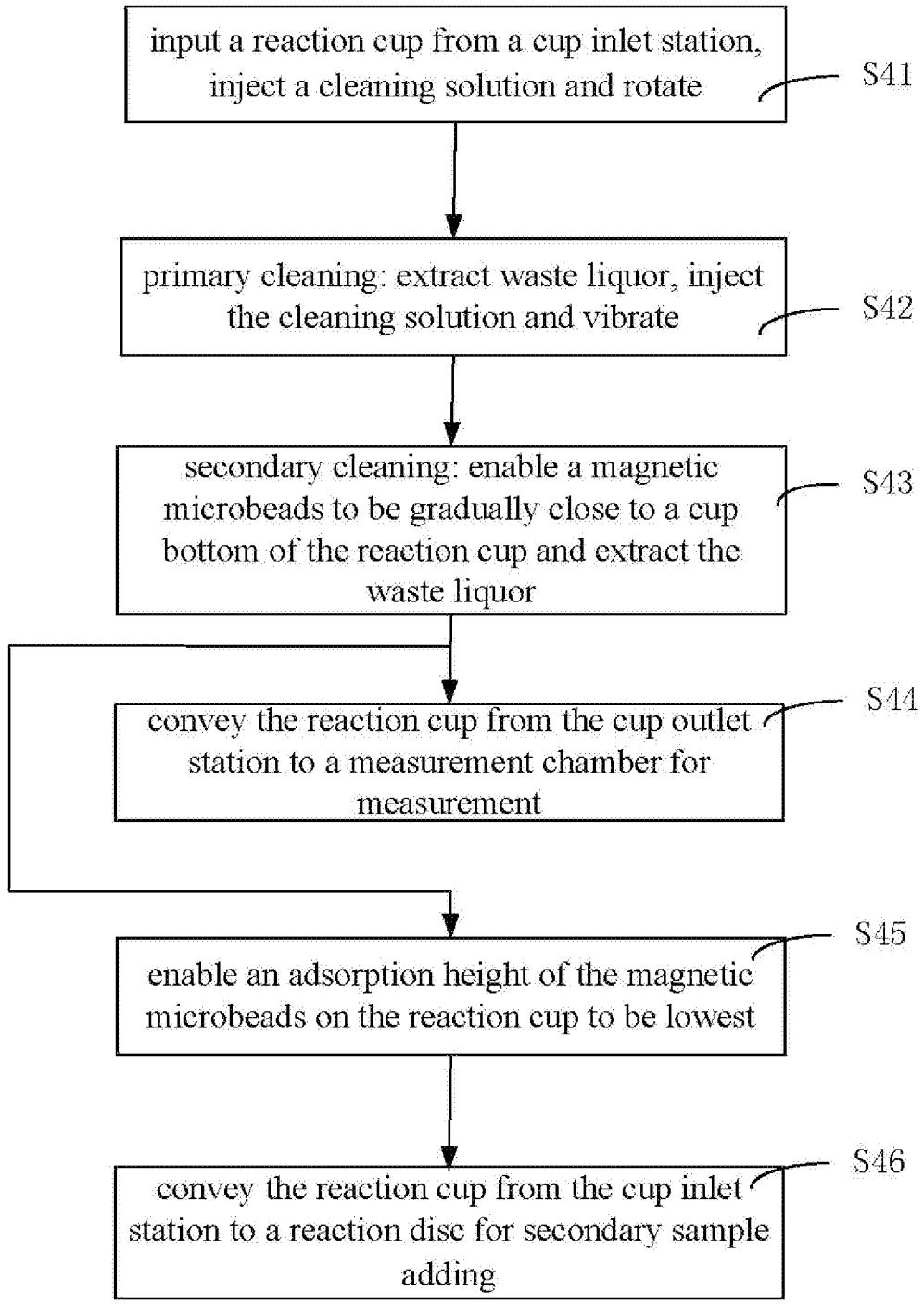
FIG. 18 is a process flowchart of a cleaning device provided by an embodiment.

Referring to FIG. 18, the first working mode mainly includes the following steps: S41, first of all, according to height of liquid level in the reaction cup, reaction cup 20 that is added with a sample for a first time and is injected with a cleaning solution may enters from a cup inlet station 11 of a cleaning device 10 and rotates around a central axis of the cleaning device 10. S42, then, primary cleaning is performed, where magnetic microbeads is adsorbed to the reaction cup 20 and waste liquor is extracted, then the cleaning solution is injected after the waste liquor is extracted and the reaction cup 20 is vibrated. S43, next, secondary cleaning is performed, where adsorption position of the magnetic microbeads on the reaction cup is enabled to gradually get close to cup bottom of the reaction cup and then the waste liquor is extracted. S44, at last, the reaction cup rotated to a cup outlet station 12 of the cleaning device 10 for a first time is conveyed to a measurement chamber.

The second working mode mainly includes the following steps: S41, first of all, according to height of liquid level in the reaction cup, reaction cup 20 that is added with a sample for a first time and is injected with a cleaning solution may enter from a cup inlet station 11 of a cleaning device 10 and rotate around a central axis of the cleaning device 10. S42, then, primary cleaning is performed, where magnetic microbeads is adsorbed to the reaction cup 20 and waste liquor is extracted, then the cleaning solution is injected after the waste liquor is extracted and the reaction cup 20 is vibrated. S43, next, secondary cleaning is performed, where adsorption position of the magnetic microbeads on the reaction cup is enabled to gradually get close to cup bottom of the reaction cup and then the waste liquor is extracted. S45, then, the distance of the adsorption position of the magnetic microbeads on the reaction cup is enabled to be lowest relative to the cup bottom of the reaction cup. S46, again, the reaction cup rotated to the cup inlet station of the cleaning device for a first time is conveyed to a reaction disc to add the sample for a second time. At last, the reaction cup 20 added with the sample for the second time enters the turntable 130 from the cup inlet station 11 of the cleaning device 10, and after the primary cleaning and the secondary cleaning are performed, the reaction cup rotated to the cup outlet station 12 of the cleaning device 10 for the second time is conveyed to a measurement chamber for measurement.

The third working mode mainly includes the following steps: S41, first of all, according to height of liquid level in the reaction cup, reaction cup 20 that is added with a sample for a first time and is injected with a cleaning solution may enters from a cup inlet station 11 of a cleaning device 10 and rotates around a central axis of the cleaning device 10. S42, then, primary cleaning is performed, where a magnetic microbeads is adsorbed to the reaction cup 20 and waste liquor is extracted, then the cleaning solution is injected after the waste liquor is extracted and the reaction cup 20 is vibrated. S43, next, secondary cleaning is performed, where adsorption position of the magnetic microbeads on the reaction cup is enabled to gradually get close to cup bottom of the reaction cup and then the waste liquor is extracted. At last, the reaction cup 20 rotates for multiple circles so that the magnetic microbeads 30 is subject to multiple times of primary cleaning and secondary cleaning; and then, the reaction cup 20 rotating to the cup outlet station 12 of the cleaning device 10 is conveyed to the measurement chamber.

Each technical characteristic of the above embodiments may be combined freely. To describe concisely, all possible combinations for the each technical characteristic of the above embodiments are not described. However, as long as there is no conflict among the combinations of these technical characteristics, all should be considered as a recording scope of the specification.

The above embodiments are only several embodiments of the present disclosure and are described concretely in detail, and therefore, should not be understood as limits to scope of the present disclosure. It should be noted that, those of ordinary skill in the part further may make several alternations and improvements without departing from the concept of the present disclosure, and all should be pertain to the scope of protection of the present disclosure. Therefore, the scope of protection of the present disclosure should be subjected to the appended claims.

What is claimed is:

1. A cleaning device, comprising a magnetic microbeads adsorption mechanism, which is configured to adsorb a magnetic microbeads in a reaction cup in a rotation movement and is provided with a cup inlet station and a cup outlet station, wherein the magnetic microbeads adsorption mechanism comprising a pedestal and a plurality of magnetic adsorption components, wherein the plurality of magnetic adsorption components are arranged at intervals on a same, mounting circumference of the pedestal; the plurality of magnetic adsorption components arranged between the cup inlet station and the cup outlet station; the mounting circumference sand, a rotation track of the reaction cup are concentrically arranged; and during a process when the reaction cup rotates from the cup inlet station to the cup outlet station passing through the plurality of magnetic adsorption components, an adsorption height of the magnetic microbeads is able to be changed;

wherein for a single reaction cup in the rotation movement, the adsorption height of the magnetic microbeads is increased first and then is decreased;

wherein each of the plurality of magnetic adsorption components comprises a plurality of arc magnets; and the plurality of arc magnets on a same magnetic adsorption component are arranged along a periphery of the mounting circumference;

wherein the plurality of magnetic adsorption components comprise a first magnetic adsorption component a middle magnetic adsorption component and a second magnetic adsorption component arranged sequentially at intervals along a rotation direction of the reaction cup; the first magnetic adsorption component is adjacent to the cup inlet station, the second magnetic adsorption component is adjacent to the cup outlet station; magnetic adsorption heights of a plurality of arc magnets of the first magnetic adsorption component are equal and are recorded as A; magnetic adsorption heights of a plurality of arc magnets of the middle magnetic adsorption component are equal and are recorded as B, and B>A;

wherein two adjacent arc magnets of the second magnetic adsorption component are spaced-apart mutually to form a gap; the second magnetic adsorption component further comprises transition magnets; and each of the transition magnets is arranged in the gap between the two adjacent arc magnets;

wherein the cleaning device further comprising a turntable, a primary cleaning mechanism and a secondary cleaning mechanism arranged on a pedestal, wherein the turntable is configured to support and drive the reaction cup to rotate; the primary cleaning mechanism comprises a plurality of primary cleaning components located above the turntable; the secondary cleaning mechanism comprises a secondary cleaning component located above the turntable; along a rotation direction of the reaction cup, each of the plurality of magnetic adsorption components is provided with a head end which the reaction cup passes first during the rotation movement and a tail end which the reaction cup passes at last during the rotation movement; the secondary cleaning component is corresponding to a tail end of the second magnetic adsorption component the plurality of primary cleaning components are corresponding to tail ends of the first magnetic adsorption component and the middle magnetic adsorption component.

2. The cleaning device as claimed in claim 1, wherein all of the plurality of magnetic adsorption components are located inside of the rotation track of the reaction cup.

3. The cleaning device as claimed in claim 1, wherein at least a reaction cup station is accommodated between two adjacent magnetic adsorption components.

4. The cleaning device as claimed in claim 1, wherein the adsorption height of the magnetic microbeads at the cup outlet station is lower than the adsorption height of the magnetic microbeads at the cup inlet station.

5. The cleaning device as claimed in claim 1, wherein each of the plurality of magnetic adsorption components further comprises a support seat and a magnetic conductive piece; the support seat is fixed on the mounting circumference of the pedestal; the magnetic conductive piece is fixed on surface, facing to the reaction cup, of the support seat; and the arc magnets are attached on a corresponding magnetic conductive piece.

6. The cleaning device as claimed in claim 1, wherein each of the plurality of arc magnets comprises a first magnet and a second magnet that are vertically overlapped; and a distance from the overlapping position of the first magnet and the second magnet to the pedestal is in direct proportion with a magnetic adsorption height of the arc magnet.

7. The cleaning device as claimed in claim 1, wherein a magnetic adsorption height of an arc magnet, which is closest to the middle magnetic adsorption component of the second magnetic adsorption component is C and the C is equal to the B.

8. The cleaning device as claimed in claim 1, wherein along the rotation direction of the reaction cup, the magnetic adsorption heights of the plurality of arc magnets of the second magnetic adsorption component are decreased, so that the adsorption height of the magnetic microbeads is decreased.

9. The cleaning device as claimed in claim 1, wherein two adjacent arc magnets which are respectively on the first magnetic adsorption component and the middle magnetic adsorption component are abutted against each other.

10. The cleaning device as claimed in claim 9, wherein along the rotation direction of the reaction cup, heights of the transition magnets are decreased.

11. The cleaning device as claimed in claim 1, wherein a number of the arc magnets of the second magnetic adsorption component is greater than a number of the arc magnets of the first magnetic adsorption component and/or the middle magnetic adsorption component.

12. The cleaning device as claimed in claim 1, further comprising a pull-down component fixed on the mounting circumference of the pedestal, wherein the pull-down component comprises a plurality of arc magnets arranged at intervals along the periphery of the mounting circumference; the pull-down component is arranged on an inferior arc, between the first magnetic adsorption component and the second magnetic adsorption component, of the mounting circumference; and magnetic adsorption heights of the plurality of arc magnets of the pull-down component are gradually decreased.

13. The cleaning device as claimed in claim 12, wherein a magnetic adsorption height of an arc magnet close to the cup inlet station of the pull-down component is lower than magnetic adsorption heights of the arc magnets of other magnetic adsorption components.

14. The cleaning device as claimed in claim 12, wherein the pull-down component further comprises transition magnets; two adjacent arc magnets of the pull-down component are spaced-apart mutually to form a gap; and each of the transition magnet is arranged in the gap.

15. The cleaning device as claimed in claim 1, further comprising locating blocks of which a number is the same as a number of the magnetic adsorption components, wherein the locating blocks are fixed on the pedestal and are opposite to the magnetic adsorption components; and the locating blocks and the magnetic adsorption components that are corresponding to each other are spaced-apart to form a channel for the reaction cup to move along the rotation track.

16. The cleaning device as claimed in claim 1, each of the primary cleaning component and the secondary cleaning component comprises a liquid extraction needle; and during liquid extraction, a position of the liquid extraction needle relative to the reaction cup is constant.

17. The cleaning device as claimed in claim 16, wherein the secondary cleaning mechanism comprises a cleaning groove; the cleaning groove is formed on the pedestal; and the liquid extraction needle after extracting the waste liquor is able to be cleaned in the cleaning groove.

18. The cleaning device as claimed in claim 16, further comprising a mixing mechanism, wherein the mixing mechanism is corresponding to a gap between two adjacent magnetic adsorption components; and the mixing mechanism is configured to vibrate the reaction cup, the mixing mechanism comprises a mixing rotor, the mixing rotor is eccentrically arranged and is able to vibrate to mix a suspension solution of the reaction cup.

19. A chemiluminescence detector, comprising the cleaning device as claimed in claim 1.

* * * * *